US009447182B2

(12) United States Patent
Brouard et al.

(10) Patent No.: US 9,447,182 B2
(45) Date of Patent: Sep. 20, 2016

(54) ANTIBODIES DIRECTED AGAINST THE ALPHA CHAIN OF IL7 RECEPTOR—THEIR USE FOR THE PREPARATION OF DRUG CANDIDATES

(71) Applicants: EFFIMUNE, Nantes (FR); INSTITUT NATIONAL DE LA SANTE ET DE LA RECHERCHE MEDICALE, Paris (FR)

(72) Inventors: Sophie Brouard, Suce sur Erdre (FR); Le Hoa Mai, Orvault (FR); Caroline Mary, Sainte-Pazanne (FR); Nicolas Poirier, Treillieres (FR); Jean-Paul Soulillou, Nantes (FR); Bernard Vanhove, Reze (FR)

(73) Assignees: OSE IMMUNOTHERAPEUTICS, Nantes (FR); INSTITUT NATIONAL DE LA SANTE ET LA RECHERCHE MEDICALE, Paris (FR)

( * ) Notice: Subject to any disclaimer, the term of this patent is extended or adjusted under 35 U.S.C. 154(b) by 20 days.

(21) Appl. No.: 14/352,992

(22) PCT Filed: Oct. 4, 2012

(86) PCT No.: PCT/EP2012/069670
§ 371 (c)(1),
(2) Date: Apr. 18, 2014

(87) PCT Pub. No.: WO2013/056984
PCT Pub. Date: Apr. 25, 2013

(65) Prior Publication Data
US 2014/0308281 A1    Oct. 16, 2014

(30) Foreign Application Priority Data

Oct. 19, 2011  (EP) .................................... 11306353

(51) Int. Cl.

| | | |
|---|---|---|
| C07K 16/00 | (2006.01) | |
| C07K 16/24 | (2006.01) | |
| C07K 16/28 | (2006.01) | |
| A61K 39/395 | (2006.01) | |
| A61K 45/06 | (2006.01) | |
| A61K 47/48 | (2006.01) | |
| A61K 39/00 | (2006.01) | |

(52) U.S. Cl.
CPC ......... *C07K 16/244* (2013.01); *A61K 39/3955* (2013.01); *A61K 45/06* (2013.01); *A61K 47/48215* (2013.01); *C07K 16/2866* (2013.01); *A61K 2039/505* (2013.01); *C07K 2317/732* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| WO | 2007/140472 A2 | 12/2007 |
|---|---|---|
| WO | 2010/017468 A1 | 2/2010 |
| WO | 2010/085643 A1 | 7/2010 |
| WO | 2011/094259 A2 | 8/2011 |
| WO | 2011/104687 A1 | 9/2011 |

OTHER PUBLICATIONS

Paul, Fundamental Immunology, 3rd Edition, 1993, pp. 292-295, under the heading "Fv Structure and Diversity in Three Dimensions".*
Rudikoff et al Proc. Natl. Acad. Sci.USA, 79(6):1979-1983, Mar. 1982.*
Colman P. M. Research in Immunology, 145:33-36, 1994.*
Janeway et al., Immunobiology, 5th Ed., Garland Science, pp. 100-105 (2001).*
Racape et al., "Interleukin 7 Receptor Alpha as a Potential Therapeutic Target in Transplantation", Archivum Immunologiae et Therapia Experimentalis, 2009, pp. 253-261.
Michel et al., "Patients with Relapsing-Remitting Multiple Sclerosis have Normal Treg Function When Cells Expressing IL-7 Receptor Alpha-Chain are Excluded from the Analysis", The Journal of Clinical Investigation, Oct. 2008, pp. 3411-3419, vol. 118 No. 10.
Liu et al., "Retraction: Crucial Role of Interleukin-7 in T Helper Type 17 Survival and Expansion in Autoimmune Disease", Nature Medicine, Dec. 2013, pp. 1673, vol. 19 No. 12.
Liu et al., "Crucial Role of Interleukin-7 in T Helper Type 17 Survival and Expansion in Autoimmune Disease", Nature Medicine, Feb. 2010, pp. 191-199 vol. 16 No. 2.
Chung et al., "Prevention of Graft-Versus-Host Disease by Anti-IL-7RAlpha Antibody", Blood Journal, Oct. 15, 2007, pp. 2803-2810, vol. 110 No. 8.
Adams et al., "Heterologous Immunity Provides a Potent Barrier to Transplantation Tolerance", The Journal of Clinical Investigation, Jun. 2003, pp. 1887-1895 vol. 111 No. 12.
Tamura et al., "Structural Correlates of an Anticarcinoma Antibody: Identification of Specificity-Determining Residues (SDRs) and Development of a Minimally Immunogenic Antibody Variant by Retention of SDRs Only", The Journal of Immunology, pp. 1432-1441, vol. 164.

* cited by examiner

*Primary Examiner* — Shulamith H Shafer
(74) *Attorney, Agent, or Firm* — Thompson Coburn LLP

(57) ABSTRACT

The invention concerns antibodies directed against CD127, I.e. the alpha chain of the receptor for interleukin7 (IL-7), especially the receptor for human IL-7 expressed on human cells (designated human IL-7R alpha or IL-7Ra) or the TSLP receptor. The antibodies of the invention have cytotoxic activity against CD127 positive cells. The invention also relates to the use of these antibodies in order to deplete subpopulations of T lymphocytes as a result of cytotoxic action of the antibodies, through ADCC and optionally through CDC. Accordingly the invention concerns the use of the antibodies in the treatment of transplant rejection, autoimmune diseases, allergic diseases, lymphoma or cancer when these pathologies are associated with CD127 positive cells.

13 Claims, 17 Drawing Sheets

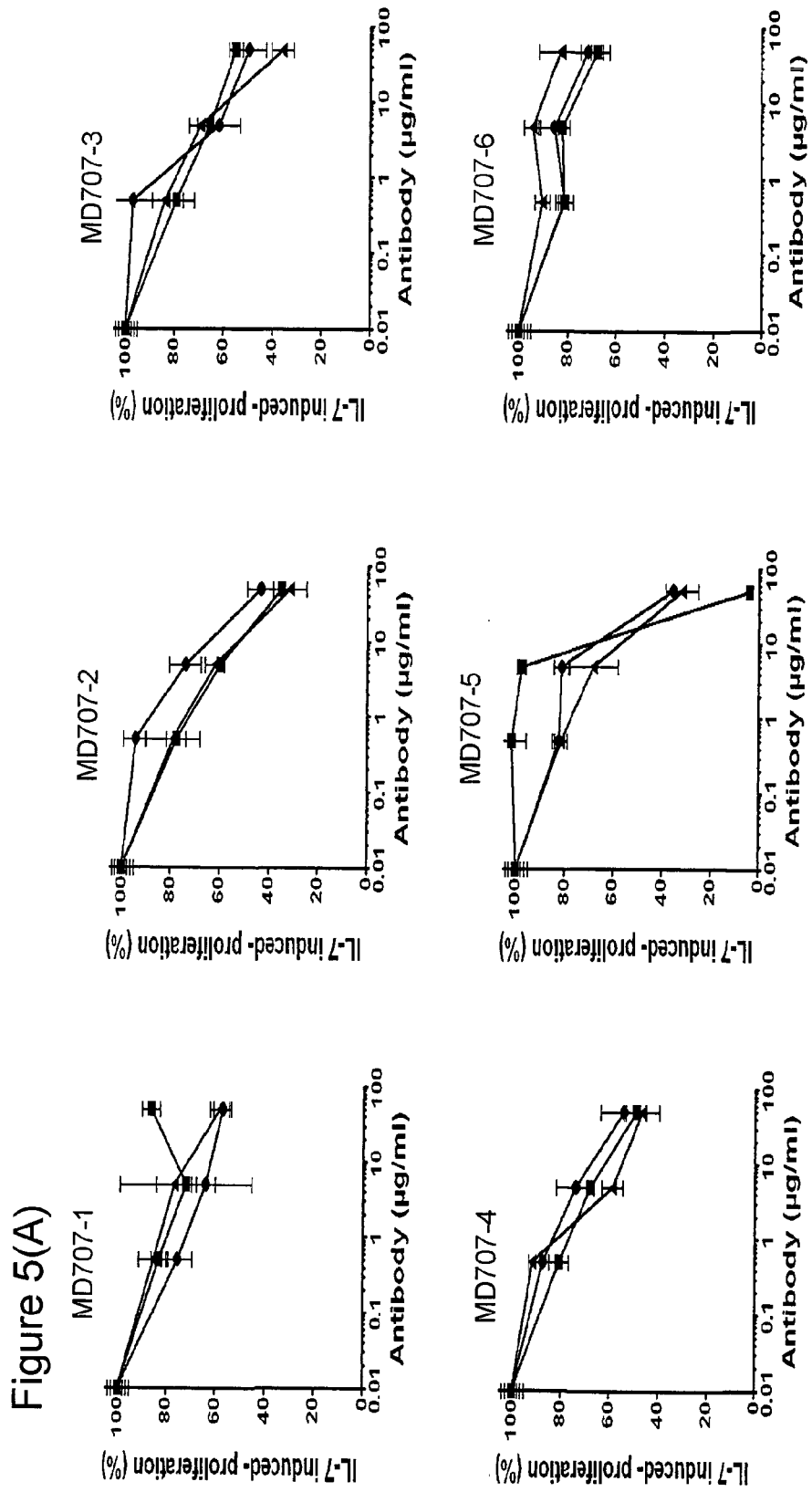

(A) MD707-1 VH

Figure 1:
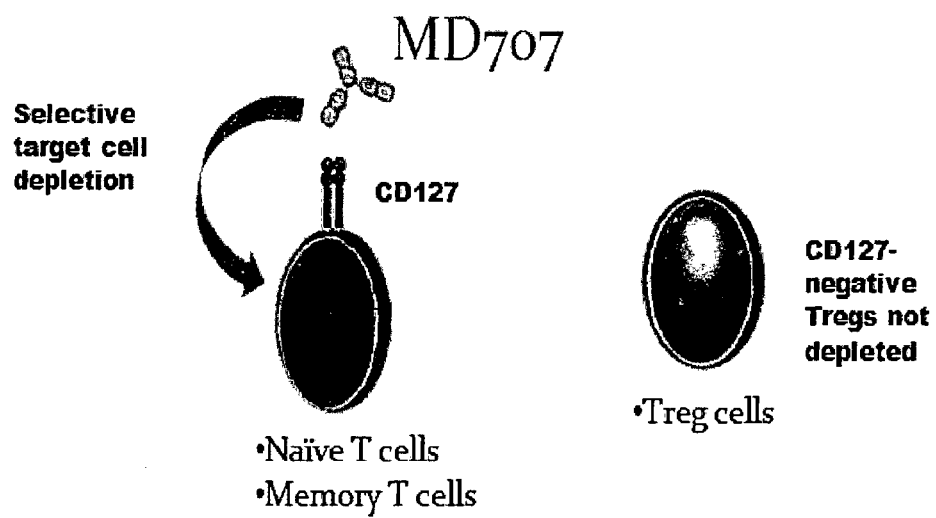
Figure 2:
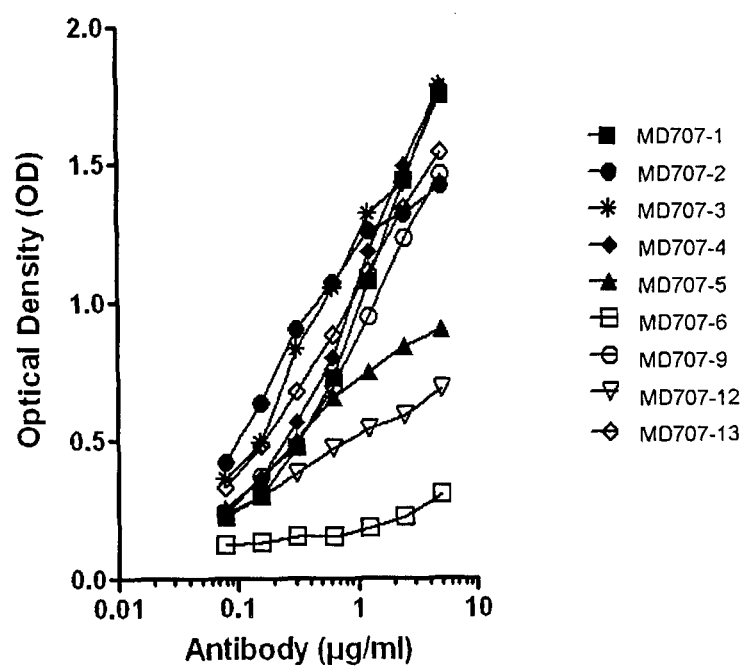

| | | | | | | | | | | | | | | | |
|---|---|---|---|---|---|---|---|---|---|---|---|---|---|---|---|
| 1 | ATG | TTG | GTG | CTG | CAG | TGG | GTT | TTG | GTG | ACT | GCT | CTT | TTT | CAA | GGT | 45 |
| 1 | Met | Leu | Val | Leu | Gln | Trp | Val | Leu | Val | Thr | Ala | Leu | Phe | Gln | Gly | 15 |

```
1    ATG TTG GTG CTG CAG TGG GTT TTG GTG ACT GCT CTT TTT CAA GGT    45
1    Met Leu Val Leu Gln Trp Val Leu Val Thr Ala Leu Phe Gln Gly    15

46   GTG CAT TGT GCG GTG CAC CTT GTT GAG TCT GGT GGA GGA TTG GTG    90
16   Val His Cys Ala Val His Leu Val Glu Ser Gly Gly Gly Leu Val    30

91   CAG CCT AAG GAG TCA TTG AAA ATC TCA TGT GCA GCC TCT GGA TTC   135
31   Gln Pro Lys Glu Ser Leu Lys Ile Ser Cys Ala Ala Ser Gly Phe    45

136  ACC TTC AGT AAT GCT GCC ATG TTC TGG GTC CGC CAG GCT CCA GGA   180
46   Thr Phe Ser Asn Ala Ala Met Phe Trp Val Arg Gln Ala Pro Gly    60

181  AAG GGT CTG GAA TGG GTT GCT CGC ATA AGA ACT AAA GCT AAT AAT   225
61   Lys Gly Leu Glu Trp Val Ala Arg Ile Arg Thr Lys Ala Asn Asn    75

226  TAT GCA ACA TAT TAT GCT GAT TCA GTG AAA GGC AGA TTC ACC ATC   270
76   Tyr Ala Thr Tyr Tyr Ala Asp Ser Val Lys Gly Arg Phe Thr Ile    90

271  TCC AGA GAT GAT TCA AAA AGC ATG GTC TAC CTA CAA ATG GAT AAC   315
91   Ser Arg Asp Asp Ser Lys Ser Met Val Tyr Leu Gln Met Asp Asn   105

316  GTG AAA ACT GAC GAC ACA GCC ATG TAT TAT TGT ATA GTA GTA GTT   360
106  Val Lys Thr Asp Asp Thr Ala Met Tyr Tyr Cys Ile Val Val Val   120

361  CTC ACA ACA ACT AGG GAC TAC TTT GAT TAC TGG GGC CAA GGA GTC   405
121  Leu Thr Thr Thr Arg Asp Tyr Phe Asp Tyr Trp Gly Gln Gly Val   135

406  ATG GTC ACA GTC TCC TCA    423
136  Met Val Thr Val Ser Ser
```

MD707-1 VL

```
1    ATG AAG TTT CCT GCT CAG TTT CTT GGA CTG ATA GTG CTC TGT ATT    45
1    Met Lys Phe Pro Ala Gln Phe Leu Gly Leu Ile Val Leu Cys Ile    15

46   CCT GGA GCC ACT GGG GAT ATT GTG TTG ACT CAA GCT CCA CTC TCT    90
16   Pro Gly Ala Thr Gly Asp Ile Val Leu Thr Gln Ala Pro Leu Ser    30

91   GTA TCT GTC ACT CCT GGA GAG TCA GCT TCC ATC TCC TGC AGG TCT   135
31   Val Ser Val Thr Pro Gly Glu Ser Ala Ser Ile Ser Cys Arg Ser    45

136  AGT CAG AGT CTG CTG ACT GTT AAG GGC ATC ACT TCC TTG TAT TGG   180
46   Ser Gln Ser Leu Leu Thr Val Lys Gly Ile Thr Ser Leu Tyr Trp    60

181  TTC CTT CAG AAG CCA GGA AAG TCT CCT CAA CTC CTG ATG TAT CGG   225
61   Phe Leu Gln Lys Pro Gly Lys Ser Pro Gln Leu Leu Met Tyr Arg    75

226  ATG TCC AAC CTT GCC TCA GGA GTT CCA GAC AGG TTT CGT GGC AGT   270
76   Met Ser Asn Leu Ala Ser Gly Val Pro Asp Arg Phe Arg Gly Ser    90

271  GGG TCA GAA ACA GAT TTT ACA CTG AAA ATC AGT AAG GTG GAG ACT   315
91   Gly Ser Glu Thr Asp Phe Thr Leu Lys Ile Ser Lys Val Glu Thr   105

316  GAG GAT GTT GGC GTT TAT TAC TGT GCA CAG TTT CTT GAG TAT CCT   360
106  Glu Asp Val Gly Val Tyr Tyr Cys Ala Gln Phe Leu Glu Tyr Pro   120

361  CAC ACG TTT GGA GCT GGG ACC AAG CTG GAA CTG AAA CGG    399
121  His Thr Phe Gly Ala Gly Thr Lys Leu Glu Leu Lys Arg
```

Figure 6A (B) >MD707-3 VH

```
1    ATG TTG GTG CTG CAG TGG GTT TTG GTG ACT GCT CTT TTT CAA GGT    45
1    Met Leu Val Leu Gln Trp Val Leu Val Thr Ala Leu Phe Gln Gly    15

46   GTG CAT TGT GCG GTG CAC CTT GTT GAG TCT GGT GGA GGA TTG GTG    90
16   Val His Cys Ala Val His Leu Val Glu Ser Gly Gly Gly Leu Val    30

91   CAG CCT AAG GAG TCA TTG AAA ATC TCA TGT GCA GCC TCT GGA TTC    135
31   Gln Pro Lys Glu Ser Leu Lys Ile Ser Cys Ala Ala Ser Gly Phe    45

136  ACC TTC AGT AAT GCT GCC ATG TAC TGG GTC CGC CAG GCT CCA GGA    180
46   Thr Phe Ser Asn Ala Ala Met Tyr Trp Val Arg Gln Ala Pro Gly    60

181  AAG GGT CTG GAA TGG GTT GCT CGC ATA AGA ACT AAA GCT AAT AAT    225
61   Lys Gly Leu Glu Trp Val Ala Arg Ile Arg Thr Lys Ala Asn Asn    75

226  TAT GCA ACA TAT TAT GCT GAA TCA GTG AAA GGC AGA TTC ACC ATC    270
76   Tyr Ala Thr Tyr Tyr Ala Glu Ser Val Lys Gly Arg Phe Thr Ile    90

271  TCC AGA GAT GAT TCA AAA AGC ATG GTC TAC CTA CAA ATG GAT AAC    315
91   Ser Arg Asp Asp Ser Lys Ser Met Val Tyr Leu Gln Met Asp Asn    105

316  GTG AAA ACT GAC GAC ACA GCC ATG TAT TAC TGT ATA GTA GTA GTT    360
106  Val Lys Thr Asp Asp Thr Ala Met Tyr Tyr Cys Ile Val Val Val    120

361  CTC ACA ACA ACT AGG GAC TAC TTT GAT TAC TGG GGC CAA GGA GTC    405
121  Leu Thr Thr Thr Arg Asp Tyr Phe Asp Tyr Trp Gly Gln Gly Val    135

406  ATG GTC ACA GTC TCC TCA    423
136  Met Val Thr Val Ser Ser
```

MD707-3 VL

```
1    ATG AAG TTT CCT GCT CAG TTT CTT GGA CTG ATA GTG CTC TGT ATT    45
1    Met Lys Phe Pro Ala Gln Phe Leu Gly Leu Ile Val Leu Cys Ile    15

46   CCT GGA GCC ACT GGG GAT ATT GTG TTG ACT CAA GCT CCA CTC TCT    90
16   Pro Gly Ala Thr Gly Asp Ile Val Leu Thr Gln Ala Pro Leu Ser    30

91   GTA TCT GTC ACT CCT GGA GAG TCA GCT TCC ATC TCC TGC AGG TCT    135
31   Val Ser Val Thr Pro Gly Glu Ser Ala Ser Ile Ser Cys Arg Ser    45

136  AGT CAG AGT CTG CTA ACT GTT AAG GGC ATC ACT TCC TTG TAT TGG    180
46   Ser Gln Ser Leu Leu Thr Val Lys Gly Ile Thr Ser Leu Tyr Trp    60

181  TTC CTT CAG AAG CCA GGA AAG TCT CCT CAA CTC CTG ATA TAT CGG    225
61   Phe Leu Gln Lys Pro Gly Lys Ser Pro Gln Leu Leu Ile Tyr Arg    75

226  ATG TCC AAC CTT GCC TCA GGA GTT CCA GAC AGG TTT CGT GGC AGT    270
76   Met Ser Asn Leu Ala Ser Gly Val Pro Asp Arg Phe Arg Gly Ser    90

271  GGG TCA GAA ACA GAT TTT ACA CTG AAA ATC AGT AAG GTG GAG ACT    315
91   Gly Ser Glu Thr Asp Phe Thr Leu Lys Ile Ser Lys Val Glu Thr    105

316  GAG GAT GTT GGC GTT TAT TAC TGT GCA CAG TTT CTT GAG TAT CCT    360
106  Glu Asp Val Gly Val Tyr Tyr Cys Ala Gln Phe Leu Glu Tyr Pro    120

361  CAC ACG TTT GGA GCT GGG ACC AAG CTG GAA CTG AAA CGG    399
121  His Thr Phe Gly Ala Gly Thr Lys Leu Glu Leu Lys Arg
```

Figure 6B

(C) MD707-13 VH

| | | | | | | | | | | | | | | | |
|---|---|---|---|---|---|---|---|---|---|---|---|---|---|---|---|
| 1 | ATG | GCT | GTC | CTG | GTG | CTG | TTG | CTC | TGC | CTG | TTG | ATA | TTT | CCA | AGC | 45 |
| 1 | Met | Ala | Val | Leu | Val | Leu | Leu | Leu | Cys | Leu | Leu | Ile | Phe | Pro | Ser | 15 |
| 46 | TGT | GTC | CTG | TCC | CAA | GTG | CAA | CTA | AAG | GAG | TCA | GGA | CCT | GGT | CTG | 90 |
| 16 | Cys | Val | Leu | Ser | Gln | Val | Gln | Leu | Lys | Glu | Ser | Gly | Pro | Gly | Leu | 30 |
| 91 | GTA | CAG | CCA | TCA | CAG | ACC | CTG | TCT | CTC | ACC | TGC | ACT | GTC | TCT | GGG | 135 |
| 31 | Val | Gln | Pro | Ser | Gln | Thr | Leu | Ser | Leu | Thr | Cys | Thr | Val | Ser | Gly | 45 |
| 136 | TTA | TCA | TTA | CCC | AAC | AAT | AAT | ATA | GCC | TGG | ATT | CGG | CAG | TCT | CCA | 180 |
| 46 | Leu | Ser | Leu | Pro | Asn | Asn | Asn | Ile | Ala | Trp | Ile | Arg | Gln | Ser | Pro | 60 |
| 181 | GGA | AAG | GGT | CTA | GAG | TGG | ATG | GGA | GTA | ATA | TGG | AGT | AAT | GGA | GAC | 225 |
| 61 | Gly | Lys | Gly | Leu | Glu | Trp | Met | Gly | Val | Ile | Trp | Ser | Asn | Gly | Asp | 75 |
| 226 | ACA | GAT | TAT | AAT | TCA | GCT | ATC | AGA | TCC | CGA | CTG | AGC | ATC | AGC | AGG | 270 |
| 76 | Thr | Asp | Tyr | Asn | Ser | Ala | Ile | Arg | Ser | Arg | Leu | Ser | Ile | Ser | Arg | 90 |
| 271 | GAC | TCC | TCG | AAG | AGC | CAA | GTC | TTC | TTA | AGG | ATG | AAC | AGT | CTG | CAA | 315 |
| 91 | Asp | Ser | Ser | Lys | Ser | Gln | Val | Phe | Leu | Arg | Met | Asn | Ser | Leu | Gln | 105 |
| 316 | TCT | GAA | GAC | ACA | GCC | ATG | TAC | TTC | TGT | GCC | AGA | GAG | GGG | ATG | ACA | 360 |
| 106 | Ser | Glu | Asp | Thr | Ala | Met | Tyr | Phe | Cys | Ala | Arg | Glu | Gly | Met | Thr | 120 |
| 361 | ACT | CTT | GAT | TAC | TGG | GGC | CAA | GGA | GTC | GTG | GTC | ACA | GTC | TCC | TCA | 405 |
| 121 | Thr | Leu | Asp | Tyr | Trp | Gly | Gln | Gly | Val | Val | Val | Thr | Val | Ser | Ser | |

MD707-13 VL

| | | | | | | | | | | | | | | | |
|---|---|---|---|---|---|---|---|---|---|---|---|---|---|---|---|
| 1 | ATG | GAT | TTT | CAG | GTG | CAG | AGT | TTC | AGC | CTC | CTG | CTA | ATC | AGT | ATC | 45 |
| 1 | Met | Asp | Phe | Gln | Val | Gln | Ser | Phe | Ser | Leu | Leu | Leu | Ile | Ser | Ile | 15 |
| 46 | ACA | GTC | ATA | GTG | TCC | AGT | GGA | GAA | ATT | GTG | CTC | ACC | CAG | TCT | CCA | 90 |
| 16 | Thr | Val | Ile | Val | Ser | Ser | Gly | Glu | Ile | Val | Leu | Thr | Gln | Ser | Pro | 30 |
| 91 | ACA | ACC | ATG | GCT | GCG | TCT | CCA | GGA | GAG | AAG | GTC | ACC | ATC | ACC | TGC | 135 |
| 31 | Thr | Thr | Met | Ala | Ala | Ser | Pro | Gly | Glu | Lys | Val | Thr | Ile | Thr | Cys | 45 |
| 136 | CGT | GCC | AGC | TCA | AGT | GTA | AGT | TAC | ATG | CAC | TGG | TTC | CAG | CAG | AAG | 180 |
| 46 | Arg | Ala | Ser | Ser | Ser | Val | Ser | Tyr | Met | His | Trp | Phe | Gln | Gln | Lys | 60 |
| 181 | TCA | GGT | TCC | TCC | CCC | AAA | CCC | TGG | ATT | TAT | GAC | TCA | TCC | GAC | CTG | 225 |
| 61 | Ser | Gly | Ser | Ser | Pro | Lys | Pro | Trp | Ile | Tyr | Asp | Ser | Ser | Asp | Leu | 75 |
| 226 | GCT | TCT | GGA | GTC | CCA | GAT | CGC | TTC | AGT | GGC | AGT | GGG | TCT | GGG | ACC | 270 |
| 76 | Ala | Ser | Gly | Val | Pro | Asp | Arg | Phe | Ser | Gly | Ser | Gly | Ser | Gly | Thr | 90 |
| 271 | TCT | TAT | TCT | CTC | ACA | ATC | AGC | TCC | ATG | GAG | GCT | GAA | GAT | GCT | GCT | 315 |
| 91 | Ser | Tyr | Ser | Leu | Thr | Ile | Ser | Ser | Met | Glu | Ala | Glu | Asp | Ala | Ala | 105 |
| 316 | ACT | TAT | TAC | TGT | CTG | CAG | AGG | AGT | AGT | TAC | CCA | CGG | ACG | TTC | GGT | 360 |
| 106 | Thr | Tyr | Tyr | Cys | Leu | Gln | Arg | Ser | Ser | Tyr | Pro | Arg | Thr | Phe | Gly | 120 |
| 361 | GGA | GGC | ACC | AAG | CTG | GAA | TTG | AAA | CGG | | | | | | | 387 |
| 121 | Gly | Gly | Thr | Lys | Leu | Glu | Leu | Lys | Arg | | | | | | | |

Figure 6C

SEQUENCE LISTING

```
<160> NUMBER OF SEQ ID NOS: 48

<210> SEQ ID NO 1
<211> LENGTH: 423
<212> TYPE: DNA
<213> ORGANISM: RAT MD707-1/VH
<220> FEATURE:
<221> NAME/KEY: CDS
<222> LOCATION: (1)..(423)

<400> SEQUENCE: 1 atg ttg gtg ctg cag tgg gtt ttg gtg act gct ctt ttt caa ggt gtg     48
Met Leu Val Leu Gln Trp Val Leu Val Thr Ala Leu Phe Gln Gly Val
1               5                   10                  15 cat tgt gcg gtg cac ctt gtt gag tct ggt gga gga ttg gtg cag cct     96
His Cys Ala Val His Leu Val Glu Ser Gly Gly Gly Leu Val Gln Pro
            20                  25                  30
```

```
aag gag tca ttg aaa atc tca tgt gca gcc tct gga ttc acc ttc agt         144
Lys Glu Ser Leu Lys Ile Ser Cys Ala Ala Ser Gly Phe Thr Phe Ser
        35                  40                  45 aat gct gcc atg ttc tgg gtc cgc cag gct cca gga aag ggt ctg gaa         192
Asn Ala Ala Met Phe Trp Val Arg Gln Ala Pro Gly Lys Gly Leu Glu
 50                  55                  60 tgg gtt gct cgc ata aga act aaa gct aat aat tat gca aca tat tat         240
Trp Val Ala Arg Ile Arg Thr Lys Ala Asn Asn Tyr Ala Thr Tyr Tyr
 65                  70                  75                  80 gct gat tca gtg aaa ggc aga ttc acc atc tcc aga gat gat tca aaa         288
Ala Asp Ser Val Lys Gly Arg Phe Thr Ile Ser Arg Asp Asp Ser Lys
                 85                  90                  95 agc atg gtc tac cta caa atg gat aac gtg aaa act gac gac aca gcc         336
Ser Met Val Tyr Leu Gln Met Asp Asn Val Lys Thr Asp Asp Thr Ala
            100                 105                 110 atg tat tat tgt ata gta gta gtt ctc aca aca act agg gac tac ttt         384
Met Tyr Tyr Cys Ile Val Val Val Leu Thr Thr Thr Arg Asp Tyr Phe
        115                 120                 125 gat tac tgg ggc caa gga gtc atg gtc aca gtc tcc tca                     423
Asp Tyr Trp Gly Gln Gly Val Met Val Thr Val Ser Ser
130                 135                 140

<210> SEQ ID NO 2
<211> LENGTH: 141
<212> TYPE: PRT
<213> ORGANISM: RAT MD707-1/VH

<400> SEQUENCE: 2

Met Leu Val Leu Gln Trp Val Leu Val Thr Ala Leu Phe Gln Gly Val
1               5                   10                  15

His Cys Ala Val His Leu Val Glu Ser Gly Gly Gly Leu Val Gln Pro
            20                  25                  30

Lys Glu Ser Leu Lys Ile Ser Cys Ala Ala Ser Gly Phe Thr Phe Ser
        35                  40                  45

Asn Ala Ala Met Phe Trp Val Arg Gln Ala Pro Gly Lys Gly Leu Glu
 50                  55                  60

Trp Val Ala Arg Ile Arg Thr Lys Ala Asn Asn Tyr Ala Thr Tyr Tyr
 65                  70                  75                  80

Ala Asp Ser Val Lys Gly Arg Phe Thr Ile Ser Arg Asp Asp Ser Lys
                 85                  90                  95

Ser Met Val Tyr Leu Gln Met Asp Asn Val Lys Thr Asp Asp Thr Ala
            100                 105                 110

Met Tyr Tyr Cys Ile Val Val Val Leu Thr Thr Thr Arg Asp Tyr Phe
        115                 120                 125

Asp Tyr Trp Gly Gln Gly Val Met Val Thr Val Ser Ser
130                 135                 140

<210> SEQ ID NO 3
<211> LENGTH: 399
<212> TYPE: DNA
<213> ORGANISM: RAT MD707-1/VL
<220> FEATURE:
<221> NAME/KEY: CDS
<222> LOCATION: (1)..(399)

<400> SEQUENCE: 3 atg aag ttt cct gct cag ttt ctt gga ctg ata gtg ctc tgt att cct          48
Met Lys Phe Pro Ala Gln Phe Leu Gly Leu Ile Val Leu Cys Ile Pro
1               5                   10                  15
```

-continued

| | |
|---|---|
| gga gcc act ggg gat att gtg ttg act caa gct cca ctc tct gta tct<br>Gly Ala Thr Gly Asp Ile Val Leu Thr Gln Ala Pro Leu Ser Val Ser<br>20                      25                      30 | 96 |
| gtc act cct gga gag tca gct tcc atc tcc tgc agg tct agt cag agt<br>Val Thr Pro Gly Glu Ser Ala Ser Ile Ser Cys Arg Ser Ser Gln Ser<br>35                      40                      45 | 144 |
| ctg ctg act gtt aag ggc atc act tcc ttg tat tgg ttc ctt cag aag<br>Leu Leu Thr Val Lys Gly Ile Thr Ser Leu Tyr Trp Phe Leu Gln Lys<br>50                      55                      60 | 192 |
| cca gga aag tct cct caa ctc ctg atg tat cgg atg tcc aac ctt gcc<br>Pro Gly Lys Ser Pro Gln Leu Leu Met Tyr Arg Met Ser Asn Leu Ala<br>65                      70                      75                      80 | 240 |
| tca gga gtt cca gac agg ttt cgt ggc agt ggg tca gaa aca gat ttt<br>Ser Gly Val Pro Asp Arg Phe Arg Gly Ser Gly Ser Glu Thr Asp Phe<br>85                      90                      95 | 288 |
| aca ctg aaa atc agt aag gtg gag act gag gat gtt ggc gtt tat tac<br>Thr Leu Lys Ile Ser Lys Val Glu Thr Glu Asp Val Gly Val Tyr Tyr<br>100                     105                    110 | 336 |
| tgt gca cag ttt ctt gag tat cct cac acg ttt gga gct ggg acc aag<br>Cys Ala Gln Phe Leu Glu Tyr Pro His Thr Phe Gly Ala Gly Thr Lys<br>115                   120                    125 | 384 |
| ctg gaa ctg aaa cgg<br>Leu Glu Leu Lys Arg<br>130 | 399 |

<210> SEQ ID NO 4
<211> LENGTH: 133
<212> TYPE: PRT
<213> ORGANISM: RAT MD707-1/VL

<400> SEQUENCE: 4

Met Lys Phe Pro Ala Gln Phe Leu Gly Leu Ile Val Leu Cys Ile Pro
1               5                   10                  15

Gly Ala Thr Gly Asp Ile Val Leu Thr Gln Ala Pro Leu Ser Val Ser
            20                  25                  30

Val Thr Pro Gly Glu Ser Ala Ser Ile Ser Cys Arg Ser Ser Gln Ser
        35                  40                  45

Leu Leu Thr Val Lys Gly Ile Thr Ser Leu Tyr Trp Phe Leu Gln Lys
    50                  55                  60

Pro Gly Lys Ser Pro Gln Leu Leu Met Tyr Arg Met Ser Asn Leu Ala
65                  70                  75                  80

Ser Gly Val Pro Asp Arg Phe Arg Gly Ser Gly Ser Glu Thr Asp Phe
                85                  90                  95

Thr Leu Lys Ile Ser Lys Val Glu Thr Glu Asp Val Gly Val Tyr Tyr
            100                 105                 110

Cys Ala Gln Phe Leu Glu Tyr Pro His Thr Phe Gly Ala Gly Thr Lys
        115                 120                 125

Leu Glu Leu Lys Arg
    130

<210> SEQ ID NO 5
<211> LENGTH: 27
<212> TYPE: DNA
<213> ORGANISM: RAT MD707-1/VHCDR1
<220> FEATURE:
<221> NAME/KEY: CDS
<222> LOCATION: (1)..(27)

<400> SEQUENCE: 5 ttc acc ttc agt aat gct gcc atg ttc                                    27

```
Phe Thr Phe Ser Asn Ala Ala Met Phe
1               5

<210> SEQ ID NO 6
<211> LENGTH: 9
<212> TYPE: PRT
<213> ORGANISM: RAT MD707-1/VHCDR1

<400> SEQUENCE: 6

Phe Thr Phe Ser Asn Ala Ala Met Phe
1               5

<210> SEQ ID NO 7
<211> LENGTH: 57
<212> TYPE: DNA
<213> ORGANISM: RAT MD707-1/VHCDR2
<220> FEATURE:
<221> NAME/KEY: CDS
<222> LOCATION: (1)..(57)

<400> SEQUENCE: 7 cgc ata aga act aaa gct aat aat tat gca aca tat tat gct gat tca      48
Arg Ile Arg Thr Lys Ala Asn Asn Tyr Ala Thr Tyr Tyr Ala Asp Ser
1               5                   10                  15 gtg aaa ggc                                                          57
Val Lys Gly <210> SEQ ID NO 8
<211> LENGTH: 19
<212> TYPE: PRT
<213> ORGANISM: RAT MD707-1/VHCDR2

<400> SEQUENCE: 8

Arg Ile Arg Thr Lys Ala Asn Asn Tyr Ala Thr Tyr Tyr Ala Asp Ser
1               5                   10                  15

Val Lys Gly

<210> SEQ ID NO 9
<211> LENGTH: 36
<212> TYPE: DNA
<213> ORGANISM: RAT MD707-1/VHCDR3
<220> FEATURE:
<221> NAME/KEY: CDS
<222> LOCATION: (1)..(36)

<400> SEQUENCE: 9 gta gtt ctc aca aca act agg gac tac ttt gat tac                      36
Val Val Leu Thr Thr Thr Arg Asp Tyr Phe Asp Tyr
1               5                   10

<210> SEQ ID NO 10
<211> LENGTH: 12
<212> TYPE: PRT
<213> ORGANISM: RAT MD707-1/VHCDR3

<400> SEQUENCE: 10

Val Val Leu Thr Thr Thr Arg Asp Tyr Phe Asp Tyr
1               5                   10

<210> SEQ ID NO 11
<211> LENGTH: 48
<212> TYPE: DNA
<213> ORGANISM: RAT MD707-1/VLCDR1
<220> FEATURE:
<221> NAME/KEY: CDS
<222> LOCATION: (1)..(48)
```

<400> SEQUENCE: 11

```
agg tct agt cag agt ctg ctg act gtt aag ggc atc act tcc ttg tat        48
Arg Ser Ser Gln Ser Leu Leu Thr Val Lys Gly Ile Thr Ser Leu Tyr
1               5                   10                  15
```

<210> SEQ ID NO 12
<211> LENGTH: 16
<212> TYPE: PRT
<213> ORGANISM: RAT MD707-1/VLCDR1

<400> SEQUENCE: 12

```
Arg Ser Ser Gln Ser Leu Leu Thr Val Lys Gly Ile Thr Ser Leu Tyr
1               5                   10                  15
```

<210> SEQ ID NO 13
<211> LENGTH: 21
<212> TYPE: DNA
<213> ORGANISM: RAT MD707-1/VLCDR2
<220> FEATURE:
<221> NAME/KEY: CDS
<222> LOCATION: (1)..(21)

<400> SEQUENCE: 13

```
cgg atg tcc aac ctt gcc tca                                            21
Arg Met Ser Asn Leu Ala Ser
1               5
```

<210> SEQ ID NO 14
<211> LENGTH: 7
<212> TYPE: PRT
<213> ORGANISM: RAT MD707-1/VLCDR2

<400> SEQUENCE: 14

```
Arg Met Ser Asn Leu Ala Ser
1               5
```

<210> SEQ ID NO 15
<211> LENGTH: 27
<212> TYPE: DNA
<213> ORGANISM: RAT MD707-1/VLCDR3
<220> FEATURE:
<221> NAME/KEY: CDS
<222> LOCATION: (1)..(27)

<400> SEQUENCE: 15

```
gca cag ttt ctt gag tat cct cac acg                                    27
Ala Gln Phe Leu Glu Tyr Pro His Thr
1               5
```

<210> SEQ ID NO 16
<211> LENGTH: 9
<212> TYPE: PRT
<213> ORGANISM: RAT MD707-1/VLCDR3

<400> SEQUENCE: 16

```
Ala Gln Phe Leu Glu Tyr Pro His Thr
1               5
```

<210> SEQ ID NO 17
<211> LENGTH: 423
<212> TYPE: DNA
<213> ORGANISM: RAT MD707-3/VH
<220> FEATURE:
<221> NAME/KEY: CDS
<222> LOCATION: (1)..(423)

<400> SEQUENCE: 17

```
atg ttg gtg ctg cag tgg gtt ttg gtg act gct ctt ttt caa ggt gtg        48
Met Leu Val Leu Gln Trp Val Leu Val Thr Ala Leu Phe Gln Gly Val
1               5                   10                  15 cat tgt gcg gtg cac ctt gtt gag tct ggt gga gga ttg gtg cag cct        96
His Cys Ala Val His Leu Val Glu Ser Gly Gly Gly Leu Val Gln Pro
            20                  25                  30 aag gag tca ttg aaa atc tca tgt gca gcc tct gga ttc acc ttc agt       144
Lys Glu Ser Leu Lys Ile Ser Cys Ala Ala Ser Gly Phe Thr Phe Ser
        35                  40                  45 aat gct gcc atg tac tgg gtc cgc cag gct cca gga aag ggt ctg gaa       192
Asn Ala Ala Met Tyr Trp Val Arg Gln Ala Pro Gly Lys Gly Leu Glu
    50                  55                  60 tgg gtt gct cgc ata aga act aaa gct aat aat tat gca aca tat tat       240
Trp Val Ala Arg Ile Arg Thr Lys Ala Asn Asn Tyr Ala Thr Tyr Tyr
65                  70                  75                  80 gct gaa tca gtg aaa ggc aga ttc acc atc tcc aga gat gat tca aaa       288
Ala Glu Ser Val Lys Gly Arg Phe Thr Ile Ser Arg Asp Asp Ser Lys
                85                  90                  95 agc atg gtc tac cta caa atg gat aac gtg aaa act gac gac aca gcc       336
Ser Met Val Tyr Leu Gln Met Asp Asn Val Lys Thr Asp Asp Thr Ala
            100                 105                 110 atg tat tac tgt ata gta gta gtt ctc aca aca act agg gac tac ttt       384
Met Tyr Tyr Cys Ile Val Val Val Leu Thr Thr Thr Arg Asp Tyr Phe
        115                 120                 125 gat tac tgg ggc caa gga gtc atg gtc aca gtc tcc tca                   423
Asp Tyr Trp Gly Gln Gly Val Met Val Thr Val Ser Ser
    130                 135                 140
```

<210> SEQ ID NO 18
<211> LENGTH: 141
<212> TYPE: PRT
<213> ORGANISM: RAT MD707-3/VH

<400> SEQUENCE: 18

```
Met Leu Val Leu Gln Trp Val Leu Val Thr Ala Leu Phe Gln Gly Val
1               5                   10                  15

His Cys Ala Val His Leu Val Glu Ser Gly Gly Gly Leu Val Gln Pro
            20                  25                  30

Lys Glu Ser Leu Lys Ile Ser Cys Ala Ala Ser Gly Phe Thr Phe Ser
        35                  40                  45

Asn Ala Ala Met Tyr Trp Val Arg Gln Ala Pro Gly Lys Gly Leu Glu
    50                  55                  60

Trp Val Ala Arg Ile Arg Thr Lys Ala Asn Asn Tyr Ala Thr Tyr Tyr
65                  70                  75                  80

Ala Glu Ser Val Lys Gly Arg Phe Thr Ile Ser Arg Asp Asp Ser Lys
                85                  90                  95

Ser Met Val Tyr Leu Gln Met Asp Asn Val Lys Thr Asp Asp Thr Ala
            100                 105                 110

Met Tyr Tyr Cys Ile Val Val Val Leu Thr Thr Thr Arg Asp Tyr Phe
        115                 120                 125

Asp Tyr Trp Gly Gln Gly Val Met Val Thr Val Ser Ser
    130                 135                 140
```

<210> SEQ ID NO 19
<211> LENGTH: 399
<212> TYPE: DNA
<213> ORGANISM: RAT MD707-3/VL
<220> FEATURE:

```
<221> NAME/KEY: CDS
<222> LOCATION: (1)..(399)

<400> SEQUENCE: 19 atg aag ttt cct gct cag ttt ctt gga ctg ata gtg ctc tgt att cct       48
Met Lys Phe Pro Ala Gln Phe Leu Gly Leu Ile Val Leu Cys Ile Pro
1               5                   10                  15 gga gcc act ggg gat att gtg ttg act caa gct cca ctc tct gta tct       96
Gly Ala Thr Gly Asp Ile Val Leu Thr Gln Ala Pro Leu Ser Val Ser
            20                  25                  30 gtc act cct gga gag tca gct tcc atc tcc tgc agg tct agt cag agt      144
Val Thr Pro Gly Glu Ser Ala Ser Ile Ser Cys Arg Ser Ser Gln Ser
        35                  40                  45 ctg cta act gtt aag ggc atc act tcc ttg tat tgg ttc ctt cag aag      192
Leu Leu Thr Val Lys Gly Ile Thr Ser Leu Tyr Trp Phe Leu Gln Lys
    50                  55                  60 cca gga aag tct cct caa ctc ctg ata tat cgg atg tcc aac ctt gcc      240
Pro Gly Lys Ser Pro Gln Leu Leu Ile Tyr Arg Met Ser Asn Leu Ala
65                  70                  75                  80 tca gga gtt cca gac agg ttt cgt ggc agt ggg tca gaa aca gat ttt      288
Ser Gly Val Pro Asp Arg Phe Arg Gly Ser Gly Ser Glu Thr Asp Phe
                85                  90                  95 aca ctg aaa atc agt aag gtg gag act gag gat gtt ggc gtt tat tac      336
Thr Leu Lys Ile Ser Lys Val Glu Thr Glu Asp Val Gly Val Tyr Tyr
            100                 105                 110 tgt gca cag ttt ctt gag tat cct cac acg ttt gga gct ggg acc aag      384
Cys Ala Gln Phe Leu Glu Tyr Pro His Thr Phe Gly Ala Gly Thr Lys
        115                 120                 125 ctg gaa ctg aaa cgg                                                   399
Leu Glu Leu Lys Arg
    130

<210> SEQ ID NO 20
<211> LENGTH: 133
<212> TYPE: PRT
<213> ORGANISM: RAT MD707-3/VL

<400> SEQUENCE: 20

Met Lys Phe Pro Ala Gln Phe Leu Gly Leu Ile Val Leu Cys Ile Pro
1               5                   10                  15

Gly Ala Thr Gly Asp Ile Val Leu Thr Gln Ala Pro Leu Ser Val Ser
            20                  25                  30

Val Thr Pro Gly Glu Ser Ala Ser Ile Ser Cys Arg Ser Ser Gln Ser
        35                  40                  45

Leu Leu Thr Val Lys Gly Ile Thr Ser Leu Tyr Trp Phe Leu Gln Lys
    50                  55                  60

Pro Gly Lys Ser Pro Gln Leu Leu Ile Tyr Arg Met Ser Asn Leu Ala
65                  70                  75                  80

Ser Gly Val Pro Asp Arg Phe Arg Gly Ser Gly Ser Glu Thr Asp Phe
                85                  90                  95

Thr Leu Lys Ile Ser Lys Val Glu Thr Glu Asp Val Gly Val Tyr Tyr
            100                 105                 110

Cys Ala Gln Phe Leu Glu Tyr Pro His Thr Phe Gly Ala Gly Thr Lys
        115                 120                 125

Leu Glu Leu Lys Arg
    130

<210> SEQ ID NO 21
<211> LENGTH: 27
```

```
<212> TYPE: DNA
<213> ORGANISM: RAT MD707-3/VHCDR1
<220> FEATURE:
<221> NAME/KEY: CDS
<222> LOCATION: (1)..(27)

<400> SEQUENCE: 21 ttc acc ttc agt aat gct gcc atg tac                         27
Phe Thr Phe Ser Asn Ala Ala Met Tyr
1               5

<210> SEQ ID NO 22
<211> LENGTH: 9
<212> TYPE: PRT
<213> ORGANISM: RAT MD707-3/VHCDR1

<400> SEQUENCE: 22

Phe Thr Phe Ser Asn Ala Ala Met Tyr
1               5

<210> SEQ ID NO 23
<211> LENGTH: 57
<212> TYPE: DNA
<213> ORGANISM: RAT MD707-3/VHCDR2
<220> FEATURE:
<221> NAME/KEY: CDS
<222> LOCATION: (1)..(57)

<400> SEQUENCE: 23 cgc ata aga act aaa gct aat aat tat gca aca tat tat gct gaa tca    48
Arg Ile Arg Thr Lys Ala Asn Asn Tyr Ala Thr Tyr Tyr Ala Glu Ser
1               5                   10                  15 gtg aaa ggc                                                 57
Val Lys Gly

<210> SEQ ID NO 24
<211> LENGTH: 19
<212> TYPE: PRT
<213> ORGANISM: RAT MD707-3/VHCDR2

<400> SEQUENCE: 24

Arg Ile Arg Thr Lys Ala Asn Asn Tyr Ala Thr Tyr Tyr Ala Glu Ser
1               5                   10                  15

Val Lys Gly

<210> SEQ ID NO 25
<211> LENGTH: 36
<212> TYPE: DNA
<213> ORGANISM: RAT MD707-3/VHCDR3
<220> FEATURE:
<221> NAME/KEY: CDS
<222> LOCATION: (1)..(36)

<400> SEQUENCE: 25 gta gtt ctc aca aca act agg gac tac ttt gat tac             36
Val Val Leu Thr Thr Thr Arg Asp Tyr Phe Asp Tyr
1               5                   10

<210> SEQ ID NO 26
<211> LENGTH: 12
<212> TYPE: PRT
<213> ORGANISM: RAT MD707-3/VHCDR3

<400> SEQUENCE: 26

Val Val Leu Thr Thr Thr Arg Asp Tyr Phe Asp Tyr
1               5                   10
```

<210> SEQ ID NO 27
<211> LENGTH: 48
<212> TYPE: DNA
<213> ORGANISM: RAT MD707-3/VLCDR1
<220> FEATURE:
<221> NAME/KEY: CDS
<222> LOCATION: (1)..(48)

<400> SEQUENCE: 27

```
agg tct agt cag agt ctg cta act gtt aag ggc atc act tcc ttg tat      48
Arg Ser Ser Gln Ser Leu Leu Thr Val Lys Gly Ile Thr Ser Leu Tyr
1               5                   10                  15
```

<210> SEQ ID NO 28
<211> LENGTH: 16
<212> TYPE: PRT
<213> ORGANISM: RAT MD707-3/VLCDR1

<400> SEQUENCE: 28

```
Arg Ser Ser Gln Ser Leu Leu Thr Val Lys Gly Ile Thr Ser Leu Tyr
1               5                   10                  15
```

<210> SEQ ID NO 29
<211> LENGTH: 21
<212> TYPE: DNA
<213> ORGANISM: RAT MD707-3/VLCDR2
<220> FEATURE:
<221> NAME/KEY: CDS
<222> LOCATION: (1)..(21)

<400> SEQUENCE: 29

```
cgg atg tcc aac ctt gcc tca                                          21
Arg Met Ser Asn Leu Ala Ser
1               5
```

<210> SEQ ID NO 30
<211> LENGTH: 7
<212> TYPE: PRT
<213> ORGANISM: RAT MD707-3/VLCDR2

<400> SEQUENCE: 30

```
Arg Met Ser Asn Leu Ala Ser
1               5
```

<210> SEQ ID NO 31
<211> LENGTH: 27
<212> TYPE: DNA
<213> ORGANISM: RAT MD707-3/VLCDR3
<220> FEATURE:
<221> NAME/KEY: CDS
<222> LOCATION: (1)..(27)

<400> SEQUENCE: 31

```
gca cag ttt ctt gag tat cct cac acg                                  27
Ala Gln Phe Leu Glu Tyr Pro His Thr
1               5
```

<210> SEQ ID NO 32
<211> LENGTH: 9
<212> TYPE: PRT
<213> ORGANISM: RAT MD707-3/VLCDR3

<400> SEQUENCE: 32

```
Ala Gln Phe Leu Glu Tyr Pro His Thr
1               5
```

<210> SEQ ID NO 33
<211> LENGTH: 405
<212> TYPE: DNA
<213> ORGANISM: RAT MD707-13/VH
<220> FEATURE:
<221> NAME/KEY: CDS
<222> LOCATION: (1)..(405)

<400> SEQUENCE: 33

```
atg gct gtc ctg gtg ctg ttg ctc tgc ctg ttg ata ttt cca agc tgt        48
Met Ala Val Leu Val Leu Leu Leu Cys Leu Leu Ile Phe Pro Ser Cys
1               5                   10                  15 gtc ctg tcc caa gtg caa cta aag gag tca gga cct ggt ctg gta cag        96
Val Leu Ser Gln Val Gln Leu Lys Glu Ser Gly Pro Gly Leu Val Gln
                20                  25                  30 cca tca cag acc ctg tct ctc acc tgc act gtc tct ggg tta tca tta       144
Pro Ser Gln Thr Leu Ser Leu Thr Cys Thr Val Ser Gly Leu Ser Leu
            35                  40                  45 ccc aac aat aat ata gcc tgg att cgg cag tct cca gga aag ggt cta       192
Pro Asn Asn Asn Ile Ala Trp Ile Arg Gln Ser Pro Gly Lys Gly Leu
        50                  55                  60 gag tgg atg gga gta ata tgg agt aat gga gac aca gat tat aat tca       240
Glu Trp Met Gly Val Ile Trp Ser Asn Gly Asp Thr Asp Tyr Asn Ser
65                  70                  75                  80 gct atc aga tcc cga ctg agc atc agc agg gac tcc tcg aag agc caa       288
Ala Ile Arg Ser Arg Leu Ser Ile Ser Arg Asp Ser Ser Lys Ser Gln
                85                  90                  95 gtc ttc tta agg atg aac agt ctg caa tct gaa gac aca gcc atg tac       336
Val Phe Leu Arg Met Asn Ser Leu Gln Ser Glu Asp Thr Ala Met Tyr
                100                 105                 110 ttc tgt gcc aga gag ggg atg aca act ctt gat tac tgg ggc caa gga       384
Phe Cys Ala Arg Glu Gly Met Thr Thr Leu Asp Tyr Trp Gly Gln Gly
            115                 120                 125 gtc gtg gtc aca gtc tcc tca                                           405
Val Val Val Thr Val Ser Ser
        130                 135
```

<210> SEQ ID NO 34
<211> LENGTH: 135
<212> TYPE: PRT
<213> ORGANISM: RAT MD707-13/VH

<400> SEQUENCE: 34

```
Met Ala Val Leu Val Leu Leu Leu Cys Leu Leu Ile Phe Pro Ser Cys
1               5                   10                  15

Val Leu Ser Gln Val Gln Leu Lys Glu Ser Gly Pro Gly Leu Val Gln
                20                  25                  30

Pro Ser Gln Thr Leu Ser Leu Thr Cys Thr Val Ser Gly Leu Ser Leu
            35                  40                  45

Pro Asn Asn Asn Ile Ala Trp Ile Arg Gln Ser Pro Gly Lys Gly Leu
        50                  55                  60

Glu Trp Met Gly Val Ile Trp Ser Asn Gly Asp Thr Asp Tyr Asn Ser
65                  70                  75                  80

Ala Ile Arg Ser Arg Leu Ser Ile Ser Arg Asp Ser Ser Lys Ser Gln
                85                  90                  95

Val Phe Leu Arg Met Asn Ser Leu Gln Ser Glu Asp Thr Ala Met Tyr
                100                 105                 110

Phe Cys Ala Arg Glu Gly Met Thr Thr Leu Asp Tyr Trp Gly Gln Gly
            115                 120                 125
```

```
Val Val Val Thr Val Ser Ser
    130             135
```

<210> SEQ ID NO 35
<211> LENGTH: 387
<212> TYPE: DNA
<213> ORGANISM: RAT MD707-13/VL
<220> FEATURE:
<221> NAME/KEY: CDS
<222> LOCATION: (1)..(387)

<400> SEQUENCE: 35

```
atg gat ttt cag gtg cag agt ttc agc ctc ctg cta atc agt atc aca      48
Met Asp Phe Gln Val Gln Ser Phe Ser Leu Leu Leu Ile Ser Ile Thr
1               5                   10                  15 gtc ata gtg tcc agt gga gaa att gtg ctc acc cag tct cca aca acc      96
Val Ile Val Ser Ser Gly Glu Ile Val Leu Thr Gln Ser Pro Thr Thr
            20                  25                  30 atg gct gcg tct cca gga gag aag gtc acc atc acc tgc cgt gcc agc     144
Met Ala Ala Ser Pro Gly Glu Lys Val Thr Ile Thr Cys Arg Ala Ser
        35                  40                  45 tca agt gta agc tac atg cac tgg ttc cag cag aag tca ggt tcc tcc     192
Ser Ser Val Ser Tyr Met His Trp Phe Gln Gln Lys Ser Gly Ser Ser
    50                  55                  60 ccc aaa ccc tgg att tat gac tca tcc gac ctg gct tct gga gtc cca     240
Pro Lys Pro Trp Ile Tyr Asp Ser Ser Asp Leu Ala Ser Gly Val Pro
65                  70                  75                  80 gat cgc ttc agt ggc agt ggg tct ggg acc tct tat tct ctc aca atc     288
Asp Arg Phe Ser Gly Ser Gly Ser Gly Thr Ser Tyr Ser Leu Thr Ile
                85                  90                  95 agc tcc atg gag gct gaa gat gct gct act tat tac tgt ctg cag agg     336
Ser Ser Met Glu Ala Glu Asp Ala Ala Thr Tyr Tyr Cys Leu Gln Arg
            100                 105                 110 agt agt tac cca cgg acg ttc ggt gga ggc acc aag ctg gaa ttg aaa     384
Ser Ser Tyr Pro Arg Thr Phe Gly Gly Gly Thr Lys Leu Glu Leu Lys
        115                 120                 125 cgg                                                                  387
Arg
```

<210> SEQ ID NO 36
<211> LENGTH: 129
<212> TYPE: PRT
<213> ORGANISM: RAT MD707-13/VL

<400> SEQUENCE: 36

```
Met Asp Phe Gln Val Gln Ser Phe Ser Leu Leu Leu Ile Ser Ile Thr
1               5                   10                  15

Val Ile Val Ser Ser Gly Glu Ile Val Leu Thr Gln Ser Pro Thr Thr
            20                  25                  30

Met Ala Ala Ser Pro Gly Glu Lys Val Thr Ile Thr Cys Arg Ala Ser
        35                  40                  45

Ser Ser Val Ser Tyr Met His Trp Phe Gln Gln Lys Ser Gly Ser Ser
    50                  55                  60

Pro Lys Pro Trp Ile Tyr Asp Ser Ser Asp Leu Ala Ser Gly Val Pro
65                  70                  75                  80

Asp Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Leu Gln Arg
            100                 105                 110

Ser Ser Tyr Pro Arg Thr Phe Gly Gly Gly Thr Lys Leu Glu Leu Lys
```

-continued

```
                     115                 120                 125
Arg

<210> SEQ ID NO 37
<211> LENGTH: 27
<212> TYPE: DNA
<213> ORGANISM: RAT MD707-13/VHCDR1
<220> FEATURE:
<221> NAME/KEY: CDS
<222> LOCATION: (1)..(27)

<400> SEQUENCE: 37 tta tca tta ccc aac aat aat ata gcc                              27
Leu Ser Leu Pro Asn Asn Asn Ile Ala
1               5

<210> SEQ ID NO 38
<211> LENGTH: 9
<212> TYPE: PRT
<213> ORGANISM: RAT MD707-13/VHCDR1

<400> SEQUENCE: 38

Leu Ser Leu Pro Asn Asn Asn Ile Ala
1               5

<210> SEQ ID NO 39
<211> LENGTH: 48
<212> TYPE: DNA
<213> ORGANISM: RAT MD707-13/VHCDR2
<220> FEATURE:
<221> NAME/KEY: CDS
<222> LOCATION: (1)..(48)

<400> SEQUENCE: 39 gta ata tgg agt aat gga gac aca gat tat aat tca gct atc aga tcc    48
Val Ile Trp Ser Asn Gly Asp Thr Asp Tyr Asn Ser Ala Ile Arg Ser
1               5                  10                  15

<210> SEQ ID NO 40
<211> LENGTH: 16
<212> TYPE: PRT
<213> ORGANISM: RAT MD707-13/VHCDR2

<400> SEQUENCE: 40

Val Ile Trp Ser Asn Gly Asp Thr Asp Tyr Asn Ser Ala Ile Arg Ser
1               5                  10                  15

<210> SEQ ID NO 41
<211> LENGTH: 24
<212> TYPE: DNA
<213> ORGANISM: RAT MD707-13/VHCDR3
<220> FEATURE:
<221> NAME/KEY: CDS
<222> LOCATION: (1)..(24)

<400> SEQUENCE: 41 gag ggg atg aca act ctt gat tac                                  24
Glu Gly Met Thr Thr Leu Asp Tyr
1               5

<210> SEQ ID NO 42
<211> LENGTH: 8
<212> TYPE: PRT
<213> ORGANISM: RAT MD707-13/VHCDR3

<400> SEQUENCE: 42
```

Glu Gly Met Thr Thr Leu Asp Tyr
1               5

<210> SEQ ID NO 43
<211> LENGTH: 30
<212> TYPE: DNA
<213> ORGANISM: RAT MD707-13/VLCDR1
<220> FEATURE:
<221> NAME/KEY: CDS
<222> LOCATION: (1)..(30)

<400> SEQUENCE: 43 cgt gcc agc tca agt gta agc tac atg cac       30
Arg Ala Ser Ser Ser Val Ser Tyr Met His
1               5                   10

<210> SEQ ID NO 44
<211> LENGTH: 10
<212> TYPE: PRT
<213> ORGANISM: RAT MD707-13/VLCDR1

<400> SEQUENCE: 44

Arg Ala Ser Ser Ser Val Ser Tyr Met His
1               5                   10

<210> SEQ ID NO 45
<211> LENGTH: 21
<212> TYPE: DNA
<213> ORGANISM: RAT MD707-13/VLCDR2
<220> FEATURE:
<221> NAME/KEY: CDS
<222> LOCATION: (1)..(21)

<400> SEQUENCE: 45 gac tca tcc gac ctg gct tct       21
Asp Ser Ser Asp Leu Ala Ser
1               5

<210> SEQ ID NO 46
<211> LENGTH: 7
<212> TYPE: PRT
<213> ORGANISM: RAT MD707-13/VLCDR2

<400> SEQUENCE: 46

Asp Ser Ser Asp Leu Ala Ser
1               5

<210> SEQ ID NO 47
<211> LENGTH: 27
<212> TYPE: DNA
<213> ORGANISM: RAT MD707-13/VLCDR3
<220> FEATURE:
<221> NAME/KEY: CDS
<222> LOCATION: (1)..(27)

<400> SEQUENCE: 47 ctg cag agg agt agt tac cca cgg acg       27
Leu Gln Arg Ser Ser Tyr Pro Arg Thr
1               5

<210> SEQ ID NO 48
<211> LENGTH: 9
<212> TYPE: PRT
<213> ORGANISM: RAT MD707-13/VLCDR3

```
<400> SEQUENCE: 48

Leu Gln Arg Ser Ser Tyr Pro Arg Thr
1               5
```

ANTIBODIES DIRECTED AGAINST THE ALPHA CHAIN OF IL7 RECEPTOR—THEIR USE FOR THE PREPARATION OF DRUG CANDIDATES

CROSS-REFERENCE TO RELATED APPLICATIONS

This application is a 35 U.S.C. §371 application of PCT/EP2012/069670 filed Oct. 4, 2012, which claims the benefit of priority to European Patent Application No. 11306353.1 filed Oct. 19, 2011, each of which is incorporated herein by reference in its entirety.

The invention concerns antibodies directed against the alpha chain of the receptor for interleukin7 (IL-7), especially the receptor for human IL-7 expressed on human cells (also designated human IL-7Ralpha or IL-7Ra). The alpha chain of the receptor for interleukin7 (IL-7) is also designated CD127.

The antibodies of the invention have cytotoxic activity against CD127 positive cells.

The invention also relates to the use of these antibodies in order to deplete subpopulations of lymphocytes, or other cell populations expressing CD127 (including T lymphocytes, B lymphocytes, NK cells and dendritic cells) as a result of cytotoxic action of the antibodies, through ADCC (Antibody-Dependent Cellular Cytotoxicity) and optionally through CDC (Complement-Dependent Cytotoxicity). Accordingly the invention concerns the use of the antibodies in the treatment of pathologic conditions involving the alteration of immune response in a human patient leading to dominant tolerogenic state or, to the contrary, lack of tolerance where control of the level of the immune response would be needed as well as destruction of malignant CD127-positive cells. The invention thus provides means suitable for use in pathologies such as those induced by transplant rejection, autoimmune diseases, lymphoma or cancer when these pathologies are associated with CD127 positive cells.

Naive T cells are partly responsible for acute rejection of transplanted organs and tissues. These cells can be controlled by current immunosuppressive drugs (calcineurin inhibitors) and by monoclonal antibodies that block costimulation (anti-adhesion, CD80/86 inhibitors). Memory T cells are also responsible for transplant rejection. Memory T cells accumulate in man due to the acquired immune history, mainly former reactions against viruses. It has been shown that memory T cells can be reactivated by alloantigens as a result of "heterologous immunity", which is the cross-reaction of our anti-viral defenses with alloantigens (Adams et al, Immunol Rev 2003, 196, 147-60). Heterologous immunity represents a potent barrier to tolerance induction since memory T cells, in contrast to naive T cells, are programmed to activate quickly, with a reduced requirement for costimulatory signals. Memory T cells may also be involved in chronic rejection. Beside their role in organ and tissue transplantation, naïve and memory T cells are also co-responsible for many autoimmune diseases. This is the case for ulcerative colitis (Shinohara et al, J. Immunol. 2011, 186: 2623-32), rheumatoid arthritis, psoriasis or graft-versus-host disease.

Furthermore, several malignant cells have been shown to display IL-7R. This is the case for Sezary cutaneous lymphoma (60% of them), or childhood acute lymphoblastic leukemia in which about 15% of the cases develop gain-of-function mutation in CD127, rendering these tumors partially IL-7 dependent (Shochat et al, J Exp Med. 2011 May 9; 208(5):901-8).

CD127 is expressed by various cells, including by both memory and naive T cells. CD127 is in particular expressed by effector T cells (Teff), including resting and memory T cells, and by immature B cells, but is especially not expressed by resting natural regulatory T cells (natural Treg). IL-7Ra is essential for promoting thymocyte differenciation and clonal expansion of lymphocytes.

The role of the IL-7/CD127 pathway in transplantation rejection has been suggested by the effect of an anti-IL-7 Mab which, when associated with costimulation blockade, prolonged heart allograft survival in mice (Wang et al, Am J Transplant 2006, 6 (12), 2851-60). The role of the IL-7/CD127 pathway in autoimmunity has also been suggested by the effect of a blocking anti-IL-7Ra Mab which prevented autoimmune experimental encephalomyelitis in mice (Liu et al, Nature Medicine 2010, 16 (2), 191-198).

The depletion of T lymphocytes has been an obvious immunosuppressive approach to counteract allograft rejection or fight autoimmunity. However, total T cell depletion might not be favorable for the induction of immunological tolerance. Targeting T cell subpopulations or selectively activated T cells, without modifying Treg cells, could constitute a pro-tolerogenic approach (Haudebourg et al Transpl Int 2009, 22 (5), 509-18). CD127 may thus be regarded as a potential attractive therapeutic target for monoclonal antibodies (Mabs) aimed at modulating immune responses since such monoclonal antibodies could have the potential of depleting effector but not regulatory lymphocytes. It has been assumed accordingly that they might show efficacy in transplantation, autoimmunity (Michel et al, J Clin Invest. 2008 October; 118(10):3411-9.) and malignancies by antagonizing access of IL-7 to IL7-R and thereby limiting T and B cell function and growth.

A therapy with a monoclonal antibody against $CD127^+$ cells with cytotoxic activity could fulfill that goal by eliminating/neutralizing naïve and memory T cells while preserving Treg cells or eliminating CD127-positive malignant cells.

In this context, monoclonal antibodies against IL-7Ra having antagonist properties toward IL-7Ra have been disclosed in WO2010/017468, with a view to treat autoimmune diseases like multiple sclerosis. The described antibodies are said to be antagonist for IL-7 binding to its receptor, and active against $T_H17$ and $T_H1$ cells expansion and survival which were said to require IL-7 interaction with their CD127 receptor.

In a publication (Racapé M. et al, Arch. Immunol. Ther. Exp., 2009, 57, 253-261) the authors analysed the interest of IL-7 receptor alpha as a potential therapeutic target in transplantation. Having reviewed the expression of IL-7Ralpha on various T cells and IL-7 responsive cells, the authors determined whether targeting memory T cells expressing IL-7Ralpha could prolong allograft survival in mice and conclude that targeting IL-7 or IL-7Ralpha would advantageously spare $T_{reg}$ cells. Among the perspectives, the authors pointed out that targeting either IL-7 or IL-7Ralpha in therapeutic treatment might have different consequences on the survival of the cells expressing CD127 and might elicit different type of lymphopenia. The question of the effects of antibodies that would be directed against IL-7Ralpha depending upon whether they would be blocking or neutralizing or cytotoxic antibodies was also posed from a conceptual point of view. The authors nevertheless did not show having obtained and assayed such antibodies and rather expressed the need for further study to assess the relevancy of the hypothesis.

In view of the drawbacks of available therapeutic approaches in immune related diseases including transplant acute or chronic rejection, and other diseases involving the IL-7/IL-7Ralpha such as different types of cancers, including some breast cancers, there is still a need for further drug candidates, especially for candidates active with respect to more selective targets for the purpose of controlling e.g. modulating immune activation in human patients.

The inventors fulfil this need in providing antibodies that have the capacity to deplete aggressive effector cells while preserving pro-tolerogenic regulatory T cells, and that have shown ability to eliminate malignant cells in CD127+ lymphoma. More generally, the inventors provide antibodies that display a cytotoxic activity against human CD127+ cells especially human CD127+ T or B cells.

The inventors provide means suitable in this context, as they obtained monoclonal antibodies against IL-7Ra that also exert a cytotoxic action against target CD127+ cells and physically reduce their number (contraction of the subpopulation). In a particular embodiment, the inventors have also obtained such antibodies that combine this property with antagonist activity toward IL-7/IL7-R interaction. These Mabs with novel mechanisms of action therefore constitute new products for evaluating therapeutic benefits of CD127 targeting.

The invention thus concerns an antibody or a functional fragment thereof which binds the alpha chain of the receptor to IL-7 (designated CD127), especially of the alpha chain of the IL-7 receptor expressed by human CD127 positive cells, and which exhibits cytotoxic activity against human T cells expressing CD127 (CD127+ cells). in particular of the IL-7 receptor expressed by human T cells, In a particular embodiment, the antibodies of the invention or their functional fragments are directed against the CD127 molecule present in the iL-7 receptor and are accordingly cytotoxic against human cells, especially human T cells expressing said receptor.

In a particular embodiment of the invention, the antibodies of functional fragments thereof target and bind the same IL7-R alpha chain when it is combined with TSLP-Receptor (also known as CCRF2; Accession Number AF338733; Reche P. A. et al J Immunol. 167(1), 336-343 (2001)) as a receptor for TSLP (Reche P. A. et al, 2001). Human TSLP (Accession number AF338732) is a factor which exerts polarization of dendritic cells, promote T and B cell proliferation and differentiation and which has been shown to play a role in skin and lung diseases (Rui et al, Ann N Y Acad. Sci. 2010, 1183: 13-24). Accordingly TSLP has been shown to associate to various pathologies including airway inflammatory disease and atopic dermatitis in human and mice (Ying S. et al (2008) J Immunol 181:2790-2798; Jariwala S P. Et al (2011) Clin Exp Allergy June 14). In addition TSLP has been shown to associate to regulation of intestinal immunity and inflammation (Taylor B C. Et al (2009) J Exp Med 206: 655-667).

A "functional fragment" of an antibody of the invention is a part of the antibody, i.e. a molecule corresponding to a portion of the structure of the antibody of the invention that exhibits antigen-binding capacity (also designated as an antigen-binding fragment) for alpha chain of the IL-7 receptor for human IL-7, possibly in its native form; such fragment especially exhibits the same or substantially the same antigen-binding capacity for said antigen compared to the antigen-binding capacity of the corresponding four-chain antibody. The antigen-binding capacity can be determined by measuring the affinity of the antibody and of the considered fragment.

Functional fragments of antibodies are fragments which comprise their hypervariable domains designated CDRs (Complementary Determining Regions) or part(s) thereof encompassing the recognition site for the antigen, i.e., IL-7Ra of human IL-7, thereby defining antigen recognition specificity. Each Light and Heavy chain (respectively VL and VH) of a four-chain immunoglobulin has three CDRs, designated VL-CDR1, VL-CDR2, VL-CDR3 and VH-CDR1, VH-CDR2, VH-CDR3, respectively.

Thus the invention relates to fragments of antibodies of the invention, which comprise or consist in all or a selection of CDRs among VL-CDR1, VL-CDR2, VL-CDR3 and VH-CDR1, VH-CDR2 and VH-CDR3 or functional portions thereof, i.e. portions that exhibit the desired binding capacity preferably with a high affinity for IL-7Ra of human IL-7.

Fragments that comprise or consist in VH-CDR3 and/or VL-CDR3 or functional portions thereof are especially preferred when CDR3 regions appear to be determinant in antigen recognition specificity.

The skilled person will be able to determine the location of the various regions/domains of antibodies by reference to the standard definitions in this respect set forth, including a reference numbering system [Martin, A. C. R. (2001) Protein Sequence and Structure Analysis of Antibody Variable Domains. In: Antibody Engineering Lab Manual, ed.: Duebel, S, and Kontermann, R., Springer-Verlag, Heidelberg] or by reference to the numbering system of Kabat (Sequences of Proteins of Immunological Interest, $4^{th}$ Ed., U.S. Department of Health and Human Services, NIH, 1987) or by application of the IMGT "collier de perle" algorithm (http://www.imgt.org/IMGTindex/Colliers.html). In this respect, for the definition of the sequences of the invention, it is noted that the delimitation of the regions/domains may vary from one reference system to another. Accordingly, the regions/domains as defined in the present invention encompass sequences showing variations in length or localization of the concerned sequences within the full-length sequence of the variable domains of the antibodies, of approximately +/−10%.

Based on the structure of four-chain immunoglobulins, functional fragments can thus be defined by comparison with sequences of antibodies in the available databases and prior art (Martin A. C. R. et al), and especially by comparison of the location of the functional domains in these sequences, noting that the positions of the framework and constant domains are well defined for various classes of antibodies, especially for IgGs, in particular for mammalian IgGs.

For illustration purpose of specific embodiments of the invention, antigen-binding fragments of an antibody that contain the variable domains comprising the CDRs of said antibody encompass Fv, dsFv, scFv, Fab, Fab', F(ab')2 which are well defined with reference to Kabat (NIH 1987), Martin A. C. R. et al and also Roitt I. et al (Fundamental and Applied Immunology MEDSI/McGraw-Hill). Fv fragments consist of the VL and VH domains of an antibody associated together by hydrophobic interactions; in dsFv fragments, the VH:VL heterodimer is stabilised by a disulphide bond; in scFv fragments, the VL and VH domains are connected to one another via a flexible peptide linker thus forming a single-chain protein. Fab fragments are monomeric fragments obtainable by papain digestion of an antibody; they comprise the entire L chain, and a VH-CH1 fragment of the H chain, bound together through a disulfide bond. The F(ab')2 fragment can be produced by pepsin digestion of an antibody below the hinge disulfide; it comprises two Fab' fragments, and additionally a portion of the hinge region of the immunoglobulin molecule. The Fab' fragments are obtainable from F(ab')2 fragments by cutting a disulfide bond in the hinge region. F(ab')2 fragments are divalent, i.e. they comprise two antigen-binding sites, like the native immunoglobulin molecule; on the other hand, Fv (a VH-VL dimmer constituting the variable part of Fab), dsFv, scFv, Fab, and Fab' fragments are monovalent, i.e. they comprise a single antigen-binding site.

These basic antigen-binding fragments of the invention can be combined together to obtain multivalent antigen-binding fragments, such as diabodies, tribodies or tetrabodies. These multivalent antigen-binding fragments are also part of the present invention.

Human cells expressing CD127 as a chain of IL-7 receptor, which are the target of the antibodies of the invention and fragments thereof, are mainly T lymphocytes and more precisely are subpopulations of effector T lymphocytes including naïve and memory T cells but are not regulatory T cells, especially not resting natural Treg. Memory T cells are generated as a result of antigen priming and mainly defined by their functional characteristics, including ability to undergo recall proliferation upon re-activation and differentiation into secondary effector and memory cells. Similarly, the targeted TSLP receptor (as a combination structure with IL7-R alpha chain) masters the regulation of T helper lymphocytes, B cells and dendritic cells differentiation.

According to an embodiment of the invention, the antibodies having "cytotoxic activity against T cells" or cytotoxic properties (cytotoxic antibodies) give rise to depletion in the effector T cell population by killing these cells and accordingly reduce the number of these cells when administered. To the contrary, these antibodies do not alter the subpopulation of regulatory T cells or do not alter it to a significant extent, allowing the Treg cells to perform their function.

In this context, in a particular embodiment, it has been observed that the ratio of regulatory T (Treg) versus effector T (Teff) cells raises following administration of cytotoxic antibodies of the invention. In a particular embodiment, the cytotoxic antibodies of the invention enable to raise said ratio of about 10% or more. In a particular embodiment, the ratio of Treg versus Teff is of about 20%.

According to a particular embodiment of the invention, the cytotoxic antibodies show Antibody-Dependant Cellular Cytotoxicity (ADCC).

ADCC properties can be evaluated in an ADCC assay such as the test described in the Examples. When the antibody is a rat antibody the effector cells used in the ADCC assay are LAK (Lymphokine-activated killer) cells of rat. When the antibodies are humanized the ADCC assay can be carried out on human LAK cells.

According to a particular embodiment of the invention, the ADCC activity of the antibodies of the invention is achieved with a concentration of antibodies of at least 10 ng/ml. ADCC may be assayed with chimeric antibodies, i.e., with antibodies the constant fragment of which (Fc) is a human Fc fragment.

When an antibody harbors ADCC activity as a result of its binding to antigen, Fc fragment may help in observing this activity.

In this regard, the invention provides in particular MD707-3 antibodies or antibodies derived from MD707-3, in particular chimeric MD707-3 antibodies having a human Fc fragment having a level of ADCC activity of at least 80%, when assessed with target cells expressing recombinant human CD127.

According to another embodiment, a cytotoxic antibody or a functional fragment thereof within the frame of the invention further has antagonist properties toward interleukin 7 (IL-7) thereby antagonizing access, i.e. binding of IL-7 to CD127 on CD127 positive cells.

"Antagonist properties" mean that antibodies or functional fragments thereof of the invention, which target the IL-7Ralpha, have the effect of preventing the accessibility of the IL-7 receptor expressed on CD127 cells, especially human effector T cells, in particular human memory T cells, for its binding partner IL-7, especially human IL-7. As a result of antagonizing binding of IL-7, the antibodies of the invention or their functional fragments lead to lymphopenia by preventing IL-7-dependent thymic T cells generation. A test for measurement of the antagonist properties of the antibodies or functional fragments thereof of the invention is described in the Examples.

The antibodies of the invention which have both cytotoxic and antagonist properties for CD127 positive cells enable cumulative effects of these properties with respect to the depletion of effector T cells, especially of memory T cells especially, thereby enabling a stronger depletion (exhaustion of the pool of CD127+ cells) and corresponding reduction in the number of target T cells. According to another embodiment of the invention, the antibody or functional fragment thereof binds to the TSLP receptor through its IL-7R alpha chain. As a consequence, the antibody or the functional fragment of antibody of the invention performs TSLP inhibition as a result of modification of the T and B cells differentiation, especially impacting the so-called TH-2 differentiation observed in some autoimmune diseases and in asthma.

An antibody or a functional fragment thereof of the invention is in particular advantageously raised against a molecule which is the CD127 expressed by human T cells, possibly raised from an immunization under the form of native polypeptide or recombinant molecule Immunization can be carried out according to the protocol disclosed in the Examples below: Recombinant CD127 Fc Chimera (10975-H03H Sino Biological, Beijing, China) was used to immunize rats such as rats of the LOU/C IgkIA strain available at the University of Louvain). Hybridoma were obtained by fusing spleen mononuclear cells with the LOU rat immunocytoma IR983F, a non-secreting and azaguanine resistant cell line, according to a previously described procedure (Chassoux et al, Immunology 1988 65 623-628). Hybridoma were first screened according to the capacity of the secreted monoclonal antibodies to bind to recombinant CD127 molecule (CD127 Fc Chimera; 10975-H03H, Sino Biological, Beijing, China). Hybridoma were then screened for the capacity of their monoclonal antibodies to bind to the CD127 expressed by human T cells.

According to a particular embodiment of the invention, a cytotoxic antibody or a functional fragment thereof is selected in the group of:

a) antibodies produced by hybridoma MD707-1 deposited at the CNCM under No I-4531 or functional fragments thereof, or;

b) antibodies expressed by recombinant eukaryotic cells which are recombined with nucleic acid molecule(s) identical to cDNA corresponding to RNA expressed in hybridoma MD707-1 deposited at the CNCM under No I-4531 that encodes an antibody of a) or a functional fragment thereof, and;

c) modified antibodies with respect to a) or b), having modified CDR regions in its Variable Heavy chain (VH) and/or in its Variable Light chain (VL), in particular keeping optionally at least one identical CDR3, CDR2 and/or CDR1 region in either of VH or VL or both, and/or having modified Framework (FR) and/or constant (CH) regions, said modified antibody having more than 70% identity, especially more than 75%, more than 80%, more then 85%, more than 90%, more than 95% or up to 99% identity over the whole length of its amino acid sequence, with the antibody of a) or b) or is a functional fragment thereof.

In another embodiment of the invention, the antibody or a functional fragment thereof is cytotoxic and antagonist with respect to IL-7 and is selected in the group of:

a) antibodies produced by hybridoma MD707-3 deposited at the CNCM under No I-4532 or hybridoma MD707-13 deposited at the CNCM under No I-4533 or functional fragments thereof, or;

b) antibodies expressed by recombinant eukaryotic cells which are recombined with nucleic acid molecule(s) identical to cDNA corresponding to RNA expressed in hybridoma MD707-3 deposited at the CNCM under No I-4532 or hybridoma MD707-13 deposited at the CNCM under No I-4533 that encodes an antibody of a) or a functional fragment thereof, and;

c) modified antibodies with respect to a) or b), having modified CDR regions in its Variable Heavy chain (VH) and/or in its Variable Light chain (VL), in particular keeping optionally at least one identical CDR3, CDR2 and/or CDR1 region in either of VH or VL or both, and/or having modified Framework (FR) and/or constant (CH) regions, said modified antibody having more than 70% identity, especially more than 75%, more than 80%, more then 85%, more than 90%, more than 95% or up to 99% identity over the whole length of its amino acid sequence, with the antibody of a) or b) or is a functional fragment thereof The deposits of hybridoma under No I-4531, I-4532 and I-4533 were made on Sep. 28, 2011 at the CNCM (Collection Nationale de Cultures de Microorganismes, Paris, France) under the provisions of the Budapest Treaty.

"Hybridoma cells" according to the invention are cells generated from fusion of antibody producing cells (B Lymphocytes) from an animal previously immunized with a selected immunogen and fusion partner which are myeloma cells enabling to provide immortality to the resulting fusion cell. Myeloma cells and antibody producing cells (B cells such as splenocytes) can be of the same origin, and are eukaryotic cells in particular mammalian cells of the same animal. They can be alternatively of different origin, thus giving rise to an heterohybridoma. Myeloma cells such as the LOU rat immunocytoma IR983F, a non-secreting and azaguanine resistant cell line are chosen among cells that fail to produce immunoglobulins in order to enable the prepared hybridoma to secrete only monoclonal antibodies of the desired specificity. Other cells suitable for promoting ADCC such as those described in the following pages for the preparation of the antibodies through expression in recombinant cells may be used instead of the rat immunocytoma. Such cells are advantageously cells having a low or no fucosylation capacity.

Preparation of hybridoma suitable for carrying out the invention is performed according to conventional techniques. Embodiments are described in detail in the Examples of the present application of which the particular disclosed features can be adapted to other cells used as fusion partners.

Particular hybridoma of the invention, useful for the preparation of the antibodies or functional fragments thereof are MD707-1 deposited at the CNCM on Sep. 28, 2011 under No I-4531 or MD707-3 deposited at the CNCM on Sep. 28, 2011 under No I-4532 or MD707-13 deposited at the CNCM on Sep. 28, 2011 under No I-4533.

In view of the teaching provided by the present invention in relation to the properties of the monoclonal antibodies obtained from the deposited hybridoma, in order to express antibodies of the invention, the skilled person will be able to use alternative technologies such as expression libraries and expression systems, followed by selection of antibodies having the structure of those secreted by the hybridoma and having its binding and neutralisation properties. cDNA libraries can adequately be prepared from the RNA expressed in hybridoma of the invention and the appropriate sequences selected and expressed.

The functional fragments of the antibody may be obtained starting from the antibody, especially by using enzymatic digestion according to well known techniques including papain or pepsin digestion, or using any appropriate cleavage technique. They may be alternatively expressed in host cells modified by recombination with nucleic acid sequences encoding the amino acid sequence of said fragments, or may be synthesized, especially chemically synthesized.

Accordingly, the antibodies of the invention, including the modified antibodies, and the functional fragments of the antibodies can also be prepared by classical genetic engineering techniques, such as those described by Sambrook et al. [Molecular Cloning, A Laboratory Manual, 2nd Ed., Cold Spring Harbor Laboratory Press, Cold Spring Harbor, N.Y., (1989), and updated versions].

In accordance to the invention, "binding" to the IL-7Ra protein refers to an antigen-antibody type interaction and reference to "specific binding" properties of the antibodies or functional fragments thereof means that the antibodies or functional fragments thereof bind to the IL-7Ra protein and furthermore do not bind or bind with a significant weaker affinity to other proteins (eg common cytokine receptor γ-chain). Binding capacity can be assayed in accordance with the tests disclosed in the Examples and in particular can be assayed by ELISA, or Western Blot analysis.

In a particular embodiment, an antibody or a functional fragment thereof according to the invention comprises in its antigen-binding site at least one of the following polypeptides:

1) MD707-1
   a) for the Variable Heavy chain:
      (i) VHCDR 1 having the amino acid sequence SEQ ID No 6,
      (ii) VHCDR 2 having the amino acid sequence SEQ ID No 8,
      (iii) VHCDR 3 having the amino acid sequence SEQ ID No 10 or,
      (iv) VH having amino acid sequence from position 19 to position 141 in SEQ ID No 2; and/or
   b) for the Variable Light chain:
      (i) VLCDR 1 having the amino acid sequence SEQ ID No 12,
      (ii) VLCDR 2 having the amino acid sequence SEQ ID No 14,
      (iii) VLCDR 3 having the amino acid sequence SEQ ID No 16 or,
      (iv) VL having amino acid sequence from position 21 to position 133 in SEQ ID No 4.
2) MD707-3
   a) for the Variable Heavy chain:
      (i) VHCDR 1 having the amino acid sequence SEQ ID No 22,
      (ii) VHCDR 2 having the amino acid sequence SEQ ID No 24, (iii) VHCDR 3 having the amino acid sequence SEQ ID No 26 or,
(iv) VH having amino acid sequence from position 19 to position 141 in SEQ ID No 18; and/or
b) for the Variable Light chain:
(i) VLCDR 1 having the amino acid sequence SEQ ID No 28,
(ii) VLCDR 2 having the amino acid sequence SEQ ID No 30,
(iii) VLCDR 3 having the amino acid sequence SEQ ID No 32 or,
(iv) VL having amino acid sequence from position 21 to position 133 in SEQ ID No 20.
3) MD707-13
a) for the Variable Heavy chain:
(i) VHCDR 1 having the amino acid sequence SEQ ID No 38,
(ii) VHCDR 2 having the amino acid sequence SEQ ID No 40,
(iii) VHCDR 3 having the amino acid sequence SEQ ID No 42 or,
(iv) VH having amino acid sequence from position 22 to position 135 in SEQ ID No 34; and/or
b) for the Variable Light chain:
(i) VLCDR 1 having the amino acid sequence SEQ ID No 44,
(ii) VLCDR 2 having the amino acid sequence SEQ ID No 46,
(iii) VLCDR 3 having the amino acid sequence SEQ ID No 48 or,
(iv) VL having amino acid sequence from position 22 to position 129 in SEQ ID No 36.

The invention also relates to the versions of the VH and VL polypeptides that encompass the signal peptide and correspond respectively to SEQ ID No 2, SEQ ID No 4, SEQ ID No 18, SEQ ID No 20, SEQ ID No 34 and SEQ ID No 36.

With a view to use the antibody of the invention or their functional fragments for administration to a human patient, it might be beneficial to derive humanized monoclonal antibodies or chimeric monoclonal antibodies and/or de-immunized antibodies, from antibodies of the invention which would be non-primate antibodies such as those illustrated in the Examples, especially to lower the immune reaction of the receiving host or patient against said antibodies. Functional fragments of these variant antibodies may be obtained also as humanized, chimeric or de-immunized variants.

An antibody or a functional fragment thereof, which is a humanized antibody is derived by substitution of amino acid residue(s) present in constant region(s) of the variable chain a non human antibody of the invention, i.e., in the framework regions of the VH and/or VL, for human amino acid residue(s) having corresponding location in human antibodies according to standard definition and numbering, wherein the substitution level is from 1% to 20%, in particular from 1% to 18% of the residues in said constant regions, i.e., framework. Said constant regions include FR regions defined in four-chain antibodies.

Particular examples of modified antibodies according to the invention encompass chimeric antibodies, humanized antibodies and/or a de-immunized antibodies.

A particular modified antibody has modified amino acid residues in the CDRs regions, said modification resulting in a de-immunisation by loss of the T cell epitopes in the variable domain of the non-human antibody. De-immunisation can be performed after determination of the T cell epitopes in the antibody variable domain, especially by in silico prediction, followed by point mutation in the sequence of the variable chains of the antibody that eliminates the functional T cell epitopes. In a preferred embodiment of the invention, the modification of the CDR(s) regions, especially of the CDR3 regions are limited to the extent necessary to de-immunisation with a view to administration to the human body, e.g. to decrease binding affinity of T cell receptors for HLA-classII/peptide complexes In a particular embodiment, the CDR3 region(s) of the VH and/or of the VL is (are) not modified. In another embodiment the FR regions and/or the CH regions are also modified, especially humanized.

Antibodies within the frame of the invention encompass accordingly an antibody based on the here above defined features, which is a humanized antibody especially one obtained by substitution of amino acid residue(s) present in constant region(s) of an antibody of the invention, for human amino acid residue(s) having corresponding location in human antibodies according to standard definition and numbering, wherein the substitution level is from 1% to 20% in particular from 1% to 18% of the residues in said framework regions, and where appropriate which is substituted for de-immunisation into some or all of the CDR(s) region(s). As mentioned above, the humanization primarily targets the Framework regions of the original antibodies. In some cases, humanization may alternatively or also concern CDR region(s) especially CDR1 and/or CDR2 region(s).

Humanization can hence be achieved considering the human germline Light chain or Heavy chain frameworks that show the highest sequence identity with the sequence of the non-human antibody or fragment, and selecting the amino acid residues, especially residues exposed at the surface in the antibody, to be substituted in said non-human antibody or fragment thereof, in order to conform to the corresponding human residue(s). In a particular embodiment some of or all the FRL and/or some of or all the FRH regions are fully human, i.e., are characteristic of human framework sequences. In another embodiment selected residues in some of all the FR regions are substituted.

Methods for humanizing antibodies are also well known in the art and are described for instance by Routledege et al. ["Reshaping antibodies for therapy", in Protein Engineering of Antibody Molecules for Prophylactic and Therapeutic Applications in Man, 13-44, Academic Titles, Nottingham, England (1993)] or by Roguska et al. Protein Engineering, 9(10), 895-904, (1996)]. These methods can also apply to antigen-binding fragments, such as scFvs.

By way of example, the method known as "resurfacing" consists in replacing the set of surface residues in the frameworks of the variable region of a nonhuman antibody with a human set of surface residues, while the method known as CDR grafting consists of transferring the CDRs from a non-human antibody into the framework regions of a human antibody. CDR grafting is generally completed by framework optimization, consisting in the replacement of some residues of the human framework, in order to optimize the binding affinity.

The step of framework optimization has been recently simplified by the use of combinatorial libraries (Rosok. et al. J. Biol. Chem. 271, 22611-22618, 1996; Baca et al. J. Biol. Chem. 272, 10678-10684, 1997).

Another recent strategy available for antibody humanization preserves only the original nonhuman CDR3 sequences of light and heavy chain while the remaining sequence is selected from naive human V gene libraries (Rader et al, Proc. Natl. Acad. ScL U.S.A. 95, 8910-8915, 1998).

According to another embodiment of the invention, the antibodies are modified and are, as a result, chimeric antibodies, comprising domains or strand(s) of amino acid residues of different antibodies, in particular antibodies obtained from different animal species, combined together in a functional antibody.

The chimeric, humanized and/or de-immunized antibodies of the invention can belong to any class of immunoglobulins, like the non modified antibodies. Preferably, they belong to a subclass of the IgG class such as IgG1, IgG2, IgG3 or IgG4.

Methods for preparing recombinant antigen-binding fragments, or chimeric antibodies by combining the variable regions of an antibody with appropriate linkers, or with the constant regions of another antibody, are well known in the art.

The antibodies of the invention are said to be monoclonal antibodies, meaning that a composition of these antibodies is homogeneous, especially identical, in terms of antigen-binding specificity and accordingly in terms of variable region composition. Hence the antibodies may qualify as monoclonal even if they are obtained by techniques alternative to the technique of hybridoma.

According to another embodiment, the invention also relates to a chimeric molecule which comprises an antibody according to any of the definition provided herein or a functional fragment thereof, wherein said monoclonal antibody or functional fragment thereof is associated with a functionally different molecule. A chimeric molecule of the invention may be either a fusion chimeric protein or a conjugate resulting from any suitable form of attachment including covalent attachment, grafting, chemical bonding with a chemical or biological group or with a molecule, such as a PEG polymer or another protective group or molecule suitable for protection against proteases cleavage in vivo, for improvement of stability and/or half-life of the antibody or functional fragment. with similar techniques, especially by chemical coupling or grafting, a chimeric molecule can be prepared with a biologically active molecule said active molecule being for example chosen among toxins, in particular *Pseudomonas* exotoxin A (Risberg et al, *PLoS One.* 2011; 6(9):e24012), the A-chain of plant toxin ricin (Van Oosterhout et al, *Int J. Pharm.* 2001 Jun. 19; 221(1-2):175-86.) or saporin toxin (Flavell et al, *Br J. Haematol.* 2006 July; 134(2):157-70)), especially a therapeutic active ingredient, a vector (including especially a protein vector) suitable for targeting the antibody or functional fragment to specific cells or tissues of the human body, or it may be associated with a label or with a linker, especially when fragments of the antibody are used.

PEGylation of the antibody or functional fragments thereof is a particular interesting embodiment as it improves the delivery conditions of the active substance to the host, especially for a therapeutic application. PEGylation can be site specific to prevent interference with the recognition sites of the antibodies or functional fragments, and can be performed with high molecular weight PEG. PEGylation can be achieved through free Cysteine residues present in the sequence of the antibody or functional fragment or through added free Cysteine residues in the amino sequence of the antibody or functional fragment.

The invention concerns also a composition comprising antibodies or functional fragments thereof as defined herein, wherein the antibodies or functional fragments thereof are a homogeneous population of antibodies or functional fragments thereof or are monoclonal antibodies or functional fragments thereof.

The invention also concerns a composition or an assembly of compounds comprising antibodies as disclosed herein, or a chimeric molecule of the invention, which comprises:

a) antibodies having both cytotoxic activity against CD127 positive cells, especially CD127+ T cells and antagonist properties toward human IL-7 or, b) a population of antibodies or functional fragments thereof having cytotoxic activity against CD127 positive cells, especially CD127+ T cells and a population of antibodies or functional fragments thereof having antagonist properties toward human IL-7, these populations of antibodies being either combined in a mixture or separated and, in this latter option, formulated for combined or sequential administration.

The definitions provided herein especially by reference to the antibodies of the invention, similarly apply to the functional fragments thereof except where it is technically obviously not relevant. These definitions also apply to molecules (in particular chimeric antibodies or chimeric molecules) or compositions comprising these antibodies or functional fragments thereof or derived from these antibodies, as disclosed in the present application. It is further specified that the functional fragments of the antibodies of the invention are derived from the antibodies from a conceptual or design point of view but may be prepared through various techniques, not necessarily having recourse to the antibodies as products.

The invention also relates to a nucleic acid molecule encoding an antibody according to any of the definitions provided herein.

Such a nucleic acid suitable for the preparation of antibodies of the invention or functional fragments thereof is especially chosen in the group of:

1) MD707-1
   i. a polynucleotide encoding the VH region having the sequence of SEQ ID No 1, or its fragment from position 55 to position 423,
   ii. a polynucleotide encoding the VL region having the sequence of SEQ ID No 3, or its fragment from position 61 to position 399,
   iii. a polynucleotide encoding the VHCDR1 region having the sequence of SEQ ID No 5,
   iv. a polynucleotide encoding the VHCDR2 region having the sequence of SEQ ID No 7,
   v. a polynucleotide encoding the VHCDR3 region having the sequence of SEQ ID No 9,
   vi. a polynucleotide encoding the VLCDR1 region having the sequence of SEQ ID No 11,
   vii. a polynucleotide encoding the VLCDR2 region having the sequence of SEQ ID No 13,
   viii. a polynucleotide encoding the VLCDR3 region having the sequence of SEQ ID No 15.
2) MD707-3
   i. a polynucleotide encoding the VH region having the sequence of SEQ ID No 17, or its fragment from position 55 to position 423,
   ii. a polynucleotide encoding the VL region having the sequence of SEQ ID No 19, or its fragment from position 61 to position 399,
   iii. a polynucleotide encoding the VHCDR1 region having the sequence of SEQ ID No 21,
   iv. a polynucleotide encoding the VHCDR2 region having the sequence of SEQ ID No 23,
   v. a polynucleotide encoding the VHCDR3 region having the sequence of SEQ ID No 25,
   vi. a polynucleotide encoding the VLCDR1 region having the sequence of SEQ ID No 27, vii. a polynucleotide encoding the VLCDR2 region having the sequence of SEQ ID No 29,
viii. a polynucleotide encoding the VLCDR3 region having the sequence of SEQ ID No 31.
3) MD707-13
i. a polynucleotide encoding the VH region having the sequence of SEQ ID No 33, or its fragment from position 64 to position 405,
ii. a polynucleotide encoding the VL region having the sequence of SEQ ID No 35, or its fragment from position 67 to position 387,
iii. a polynucleotide encoding the VHCDR1 region having the sequence of SEQ ID No 37,
iv. a polynucleotide encoding the VHCDR2 region having the sequence of SEQ ID No 39,
V. a polynucleotide encoding the VHCDR3 region having the sequence of SEQ ID No 41,
vi. a polynucleotide encoding the VLCDR1 region having the sequence of SEQ ID No 43,
vii. a polynucleotide encoding the VLCDR2 region having the sequence of SEQ ID No 45,
viii. a polynucleotide encoding the VLCDR3 region having the sequence of SEQ ID No 47.

According to a particular embodiment of the invention, polynucleotides have modified nucleotides with respect to the sequence of SEQ ID No 1, SEQ ID No 3, SEQ ID No 5, SEQ ID No 7, SEQ ID No 9, SEQ ID No 11, SEQ ID No 13, SEQ ID No 15, SEQ ID No 17, SEQ ID No 19, SEQ ID No 21, SEQ ID No 23, SEQ ID No 25, SEQ ID No 27, SEQ ID No 29, SEQ ID No 31, SEQ ID No 33, SEQ ID No 35, SEQ ID No 37, SEQ ID No 39, SEQ ID No 41, SEQ ID No 43, SEQ ID No 45, and/or SEQ ID No 47 and,
a) either encode a polypeptide having amino acid sequence of respectively SEQ ID No 2 or its fragment from position 19 to position 141, SEQ ID No 4 or its fragment from position 21 to position 133, SEQ ID No 6, SEQ ID No 8, SEQ ID No 10, SEQ ID No 12, SEQ ID No 14, SEQ ID No 16, SEQ ID No 18 or its fragment from position 19 to position 141, SEQ ID No 20 or its fragment from position 21 to position 133, SEQ ID No 22, SEQ ID No 24, SEQ ID No 26, SEQ ID No 28, SEQ ID No 30, SEQ ID No 32, SEQ ID No 34 or its fragment from position 22 to position 135, SEQ ID No 36 or its fragment from position 22 to position 129, SEQ ID No 38, SEQ ID No 40, SEQ ID No 42, SEQ ID No 44, SEQ ID No 46, and/or SEQ ID No 48 and/or
b) have at least 85%, preferably at least 90%, more preferably at least 95%, and most preferably at least 98% or at least 99% identity over their whole length with one of the polynucleotides having sequence of SEQ ID No 1 or its fragment from position 55 to position 423, SEQ ID No 3 or its fragment from position 61 to position 399, SEQ ID No 5, SEQ ID No 7, SEQ ID No 9, SEQ ID No 11, SEQ ID No 13, SEQ ID No 15, SEQ ID No 17 or its fragment from position 55 to position 423, SEQ ID No 19 or its fragment from position 61 to position 399, SEQ ID No 21, SEQ ID No 23, SEQ ID No 25, SEQ ID No 27, SEQ ID No 29, SEQ ID No 31, SEQ ID No 33 or its fragment from position 64 to position 405, SEQ ID No 35 or its fragment from position 67 to position 387, SEQ ID No 37, SEQ ID No 39, SEQ ID No 41, SEQ ID No 43, SEQ ID No 45, and/or SEQ ID No 47.

Another polynucleotide of the invention is a fragment of the polynucleotide having sequence of SEQ ID No 1, SEQ ID No 3, SEQ ID No 5, SEQ ID No 7, SEQ ID No 9, SEQ ID No 11, SEQ ID No 13, SEQ ID No 15, SEQ ID No 17, SEQ ID No 19, SEQ ID No 21, SEQ ID No 23, SEQ ID No 25, SEQ ID No 27, SEQ ID No 29, SEQ ID No 31, SEQ ID No 33, SEQ ID No 35, SEQ ID No 37, SEQ ID No 39, SEQ ID No 41, SEQ ID No 43, SEQ ID No 45, and/or SEQ ID No 47 and encodes a functional fragment of a polypeptide having amino acid sequence of respectively SEQ ID No 2, SEQ ID No 4, SEQ ID No 6, SEQ ID No 8, SEQ ID No 10, SEQ ID No 12, SEQ ID No 14, SEQ ID No 16, SEQ ID No 18, SEQ ID No 20, SEQ ID No 22, SEQ ID No 24, SEQ ID No 26, SEQ ID No 28, SEQ ID No 30, SEQ ID No 32, SEQ ID No 34, SEQ ID No 36, SEQ ID No 38, SEQ ID No 40, SEQ ID No 42, SEQ ID No 44, SEQ ID No 46, and/or SEQ ID No 48.

Polynucleotides of the invention can be optimized sequences, especially for the expression in host cells. Optimisation techniques in this field are conventional one.

For the purpose of recovery of the antibodies of the invention from producing cells the polynucleotide may comprise, upstream from the nucleotide sequence encoding the antibody chains, a sequence encoding a signal peptide for secretion of the expressed antibody.

Polynucleotide fragment above have advantageously a sequence of at least 9 nucleotides and are shorter than their sequence of origin.

According to a particular embodiment, polynucleotides of the invention may advantageously comprise, besides a sequence encoding an antibody or a functional fragment thereof according to the invention, or a chimeric molecule including the same as disclosed herein, a sequence encoding a signal peptide allowing secretion of said protein when expressed in a production cell. They may also comprise one or more sequence(s) encoding one or more marker peptide(s) for detecting, and/or facilitating the purification of, said protein.

The invention also concerns a vector for the cloning and/or for the expression of a polynucleotide disclosed herein, and is especially a plasmid suitable for cloning and/or expressing in mammalian cells, which comprises regulation sequences for transcription and expression.

The invention further relates to cells or cell lines recombined with a polynucleotide of the invention, especially a mammalian or an avian cell or cell line. For example Chinese Hamster Ovary Cells, genetically modified to reduce global fucosylation. Indeed, Antibodies lacking core fucosylation show a significantly enhanced antibody-dependent cell-mediated cytotoxicity (ADCC) (von Horsten et al, Glycobiology. 2010 December; 20(12):1607-18). Another example is the EB66 cell line which naturally has low fucosylation properties (Olivier et al, MAbs. 2010 Jul. 16; 2(4)).

Thus the invention also relates to a method of preparing an antibody or a functional fragment thereof, which comprises:
a) obtaining a hybridoma after immunizing an animal, especially a mammal with the human alpha chain of the human IL-7 receptor and, where necessary, boosting said animal with the same immunogen, recovering spleen or lymph node cells from the animal responding to immunization and fusing said cells with myeloma cells to isolate monoclonal antibodies and
b) expressing genes coding for such antibodies in the recombinant form in cells that present a low or absent fucosylation capacity, such as EB66 avian cells, in conditions enabling the recovery of antibodies, and
c) recovering the antibodies having the desired binding affinity against the alpha chain of the human IL-7 receptor.

Another object of the invention is a pharmaceutical composition comprising an antibody or a functional fragment thereof or a chimeric molecule, according to the invention, with a pharmaceutical vehicle, wherein said pharmaceutical composition optionally further comprises a different active ingredient.

The invention also relates to a composition comprising as an active ingredient, an antibody or a functional fragment thereof or a chimeric molecule according to the definitions provided herein or a pharmaceutical composition, in a formulation suitable for controlling human CD127 positive cells survival or expansion, in particular human CD127 positive effector cells, especially CD127+ memory T cells survival or expansion, especially memory T cells which are both CD127+ and CD8+, or which are both CD127+ and CD4+ cells, when administered to a human patient.

A composition of the invention may further comprise an additional compound having a therapeutic immunomodulator effect, in particular on cells involved in allergy or autoimmunity. For illustration purpose immunomodulators of interest are other monoclonal antibodies targeting T cells, such as anti-CD3, anti-ICOS or anti-CD28 antibodies or recombinant proteins or antibodies targeting accessory cells such as CTLA4Ig or anti-CD40 antibodies.

The invention concerns also an antibody or a functional fragment thereof or a chimeric molecule as defined or illustrated herein, for use as active ingredient in a combination or add-on therapeutic regimen in a patient in need thereof.

An antibody or a functional fragment thereof or a chimeric molecule according to the invention, a pharmaceutical composition or a composition as defined herein are in particular proposed for use in a human patient for treating pathologic conditions influenced by immune responses, especially by memory T cells responses. Accordingly, the inventors proposed that the antibody or functional fragment thereof, chimeric molecule according to the invention, pharmaceutical composition or composition as defined herein be used for preventing organ or tissue transplant rejection or for the treatment of autoimmune or allergic diseases or a for the treatment of a cancer such as breast cancer associated with CD127+ cells, or for the treatment of a T cell cutaneous lymphoma, such as Sezary lymphoma, or for the treatment of the acute lymphoblastoid leukemia with gain-mutation of the IL7-R/TSLP pathway. By interacting with TSPLR the antibodies or functional fragments of the invention can also inhibit allergic reaction such as asthma.

By "treatment" or "therapeutic treatment", it is meant that the performed steps of administration result in improving the clinical condition of an animal or a human patient in need thereof, who suffers from disorder(s) associated with the IL-7 pathway, i.e; involving the activation or proliferation of CD127 positive cells. Such treatment aims at improving the clinical status of the animal or human patient, by eliminating or lowering the symptoms associated with the disorder(s) related to the IL-7 or TSLP. pathway, i.e; involving the activation or proliferation of CD127 positive cells and/or in a preferred embodiment, restoring to health.

Additional features and properties of the invention will be apparent from the Examples and figures which follow.

LEGEND OF THE FIGURES

FIG. 1

Selective depletion of naïve and memory T cells with MD707.

FIG. 2

ELISA profile of rat anti-human CD127 antibodies on plate coated with recombinant human IL-7 receptor at 5 μg/ml.

FIG. 3

Cross-reactivity of rat anti-human CD127 antibodies analyzed by flow cytometry on human peripheral blood mononuclear cells (PBMCs), baboon PBMCs, macaque PBMCs and rat spleen cells. MFI: Median Fluorescence Intensity. The coordinates on the abissa are $10^1$, $10^2$, $10^3$, $10^4$, $10^5$.

FIG. 4

Antibody-dependent cellular cytotoxicity (ADCC) of rat anti-human CD127 antibodies after 4 h incubation with rat lymphokine-activated killer (LAK) cells as effector (E) cells and 51Cr-labled human T lymphocytes as target (T) cells at different ratio: E:T=30:1 (square), E:T=10:1 (triangle), E:T=3:1 (round) and E:T=1:1 (diamond). Percentage of specific cytotoxicity was determined by 51Cr release.

FIG. 5

Inhibition of IL-7-induced proliferation by rat anti-human CD127 antibodies. Human T lymphocytes were incubated with antibodies for 3 days on OKT3-coated plate (1 μg/ml) and soluble recombinant human IL-7 protein (rhIL-7; Sino Biologicals, Beijing, China; reference 10975-H08H) at 100 UI/ml (square), 50 UI/ml (round) or 10 UI/ml (triangle). Proliferation was determined during the last 8 hours of incubation by incorporation of 3H-thymidine (1 μCi/wells). Proliferation of human T cells incubated in the absence of anti-CD127 antibodies on OKT3-coated plate with rhIL-7 was about $10^5$ counts per minutes (cpm).

FIG. 6

Amino acids and nucleotidic sequences of VH and VL variable domains of MD707-1 (VH SEQ ID NO: 1 and VL SEQ ID NO: 3), MD707-3 (VH SEQ ID NO: 17 and VL SEQ ID NO: 19) and MD707-13 (VH SEQ ID NO: 33 and VL SEQ ID NO: 35). The nucleic acid sequence encoding the signal peptide in each variable fragment is underlined. The amino acid sequences of respectively CDR1, CDR2 and CDR3 domains in each of the VH and VL for MD707-1, MD707-3 and MD707-13 are underlined, in accordance with the sequences disclosed as SEQ IDs. The nucleic acid sequences encoding these CDR sequences are therefore located in line with the underlined amino acid sequences in the figure.

FIG. 7

8 week-old male Balb/c mice received either anti-IL-7Ra mAb (clone A7R34) 400 μg IP every other day for 21 days (n=5) or isotype control at the same schedule (n=5). Mice were sacrificed at day 21; blood and spleen were harvested for absolute T lymphocyte counting by conventional microscopy with a Malassez device.

FIG. 8

8 week-old male Balb/c mice received either anti-IL-7Rα mAb (clone A7R34) 400 μg IP every other day for 21 days (n=5) or isotype control at the same schedule (n=5). Mice were sacrificed at day 21; mesenteric lymph nodes, and spleen were harvested for lymphocyte phenotyping by flow cytometry. Anti-IL-7Rα-treated mice had significantly higher CD3+CD4+CD25+FOXP3+ regulatory T cell frequency than control mice either in the lymph nodes (21.4 vs 12.5%) or in the spleen (20.3 vs 11.6% of CD4+ T cells) ($p<0.01$).

FIG. 9

7 to 9 week-old male Balb/c mice (H-2b) were rendered diabetic by streptozotocin 250 mg/kg IP 5-10 days before graft. Each recipient received about 500 islets isolated from 7 to 9 week-old male C57BL/6 mice (H-2d). Control group received no treatment; treated group received anti-IL-7Rα monoclonal antibody (clone A7R34) 400 μg IP every other day started from 21 days before graft and continued to post-transplant day 90. Control mice had median graft survival of 21 days (range: 14-34 days) whereas 5 of 6 treated mice had indefinite graft survival (>160 days) (p=0.0002, log-rank test).

FIG. 10

Female non-obese diabetic (NOD) mice 6 weeks of age were purchased from Charles-River France and maintained in our animal facilities. Blood glucose were measured every week from 10 weeks of age. Treatment group received anti-IL-7Rα monoclonal antibody (clone A7R34) 400 μg IP 3 times per week for 8 wks from week 8 to week 16 of age. Control group received PBS at the same volume and same schedule. At 52 weeks of age, ⅝ (62.5%) of control mice develop diabetes, whereas ⅛ treated mice has diabetes (p=0.028, log-rank test).

FIG. 11

Antibody-dependent cellular cytotoxicity (ADCC) of chimeric clone 3 anti-human CD127 antibody on mouse BA/F3 cell line transfected with human CD127. Human NK cells used as effector (E) were incubated for 4 hours with $^{51}$Cr-labled mouse BA/F3 CD127-transfected cells as target (T) cells at different ratio: E:T=3:1 (round), 10:1 (triangle) or 30:1 (square) and different concentration of chimeric MD707-3. Percentage of specific cytotoxicity was determined by $^{51}$Cr release.

FIG. 12

Antibody-dependent cellular cytotoxicity (ADCC) of chimeric clone 3 anti-human CD127 antibody on human T-cell acute lymphoblastic leukemia (T-ALL) cell lines. Human NK cells used as effector (E) were incubated for 4 hours with two different $^{51}$Cr-labled T-ALL cell lines as target (T) cells at different ratio: E:T=1:1 (round), 3:1 (triangle) or 10:1 (square) and different concentration of chimeric MD707-3. Percentage of specific cytotoxicity was determined by $^{51}$Cr release. A/Target cells were the DND41 T-ALL cell line which over-express CD127, B/Target cells were the Jurkat T-ALL cell line which express low level of CD127.

EXAMPLES

I) Preparation and Characterisation of Monoclonal Antibodies

1. Preparation and Selection of Novel Anti-Human CD127 Mabs

Rats were immunized with recombinant hCD127-Ig (hCD127 fused with a constant fragment of an immunoglobulin—Sino Biologicals, Beijing, China; reference 10975-H03H) and monoclonal antibodies were derived according to conventional techniques. The immunization protocol used was as follows: recombinant CD127 Fc Chimera (10975-H03H Sino Biological, Beijing, China) was used to immunize rats of the LOU/C IgkIA strain. Fifty micrograms of proteins were suspended in Complete Freund Adjuvant and administered s.c. After 20 days, a recall injection of the protein suspended in Incomplete Freund Adjuvant was performed. Another similar recall injection was performed on days 60 and a boost injection was performed on day 90 with 100 micrograms proteins, 4 days before spleen cells collection.

Hybridoma were obtained by fusing spleen mononuclear cells with the LOU rat immunocytoma IR983F, a non-secreting and azaguanine resistant cell line, according to a previously described procedure (Chassoux et al, Immunology 1988 65 623-628). Hybridoma were first screened according to the capacity of the secreted monoclonal antibodies to bind to recombinant CD127 molecule (CD127 Fc Chimera; 10975-H03H, Sino Biological, Beijing, China). Hybridoma were then screened for the capacity of their monoclonal antibodies to bind to the CD127 expressed by human T cells.

Thirteen clones were first selected based on the recognition by secreted antibodies of recombinant CD127 (Sino Biologicals) among which 9 were further selected on the recognition of CD127 expressed by human T cells Antibodies were produced and their isotype were characterized as well as their affinities by Surface Plasmon Resonance measurement using BIAcore technology (Table 1).

TABLE 1

Isotypes and affinities of anti-CD127 Mabs

| | | Biacore | | |
|---|---|---|---|---|
| clones | Isotype | association (Kon) | dissociation (Koff) | Biacore (Kd) |
| MD707-1 | G2a | 3.64E+04 | 5.78E−04 | 1.59E−08 |
| MD707-2 | G1 | 2.90E+05 | 1.81E−04 | 6.24E−10 |
| MD707-3 | G2a | 4.89E+04 | 3.19E−04 | 6.52E−09 |
| MD707-4 | G2a | 1.72E+04 | 1.11E−04 | 6.54E−09 |
| MO707-5 | G1 | 2.66E+05 | 6.78E−04 | 2.55E−09 |
| MD707-6 | G1 | 3.02E+04 | 1.29E−04 | 4.27E−09 |
| MD707-9 | G1 | 4.23E+04 | 3.84E−05 | 9.08E−10 |
| MD707-12 | G1 | 1.30E+05 | 2.58E−04 | 1.98E−09 |
| 7MD07-13 | G1 | 6.82E+04 | 8.91E−05 | 1.31E−09 | rCD127 Recognition of Anti-h-CD127 Mabs Assessed by ELISA

Recombinant hCD127 (Sino Biologicals, Beijing, China; reference 10975-H08H) was immobilized on plastic and increasing doses of Mabs were added to measure binding. After incubation and washing, peroxidase-labeled anti-rat immunoglobulin antibodies were added and revealed by conventional methods. Results revealed a better binding of MD707-1, 2, 3, 4, 9, 13, an intermediate binding of MD707-5 and 12, and a weak binding of MD707-6

Cross Reactivity of Anti-Human CD127 Mabs with Non-Human Primates

Figure 3A:
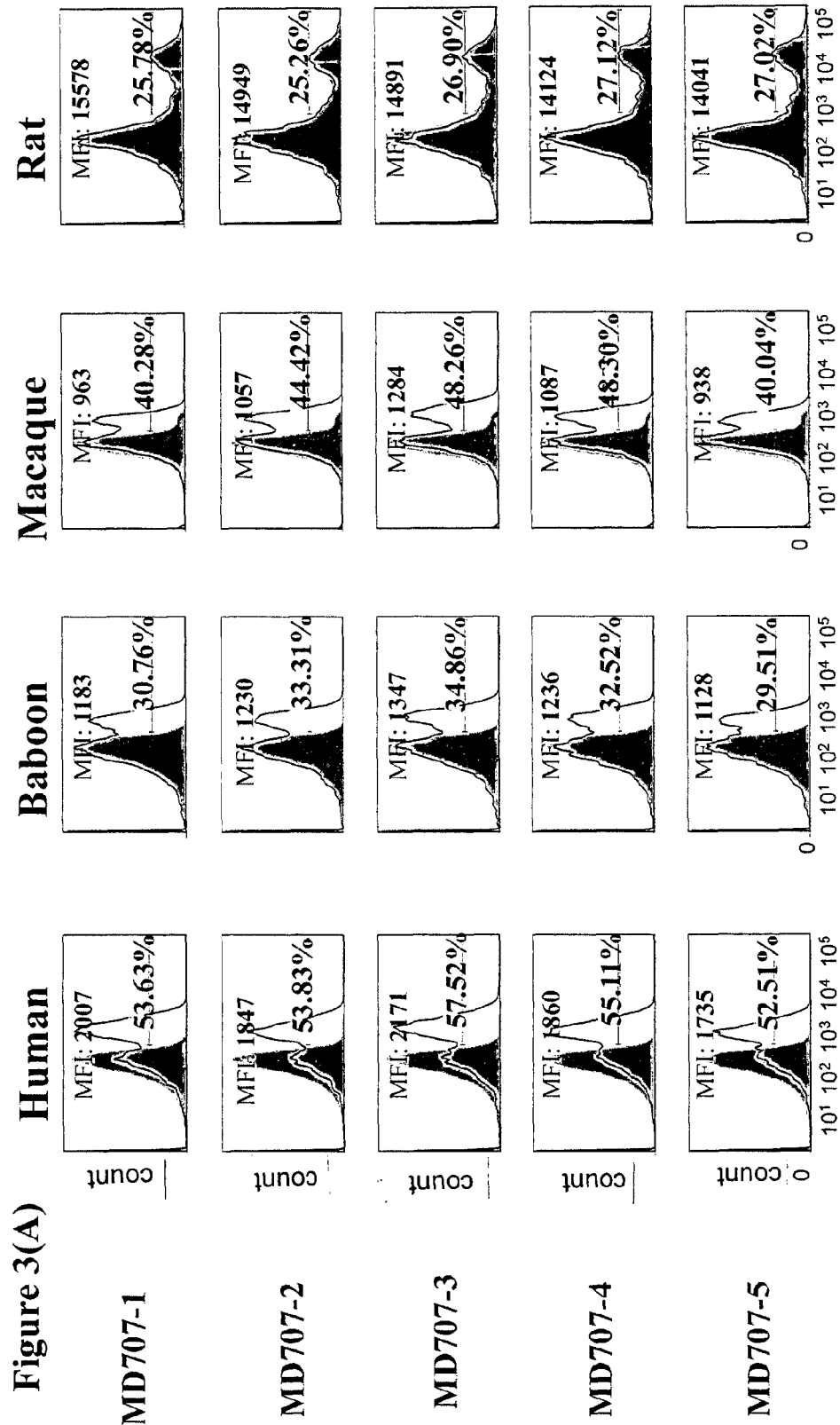
Figure 3:
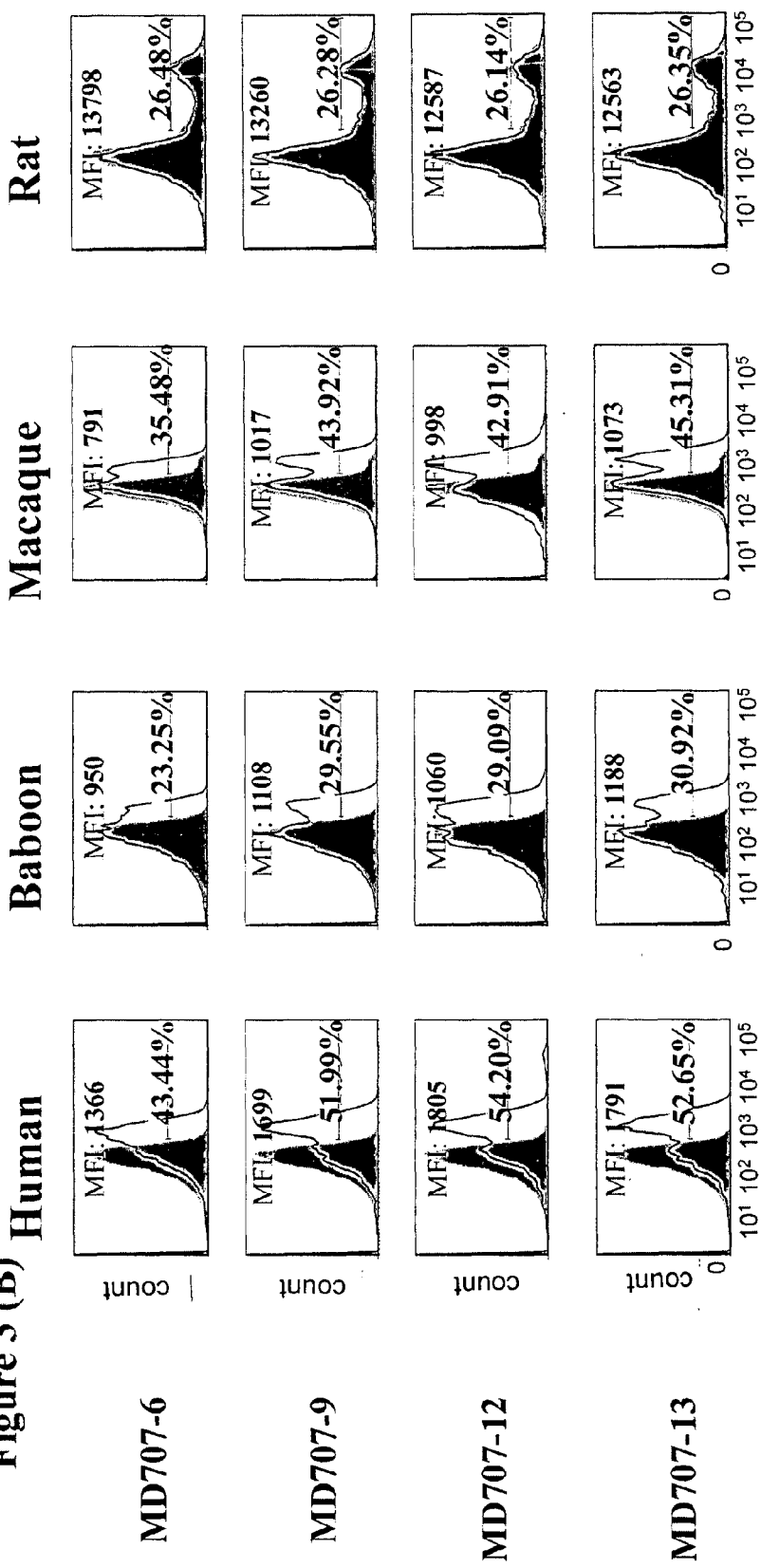

Mabs shown in table 1 were used in flow cytometry assays to study binding on primate T cells in comparison with human T cells. Rat T cells were used as a negative control, since it is unexpected that Mabs of rat origin recognize rat molecules. The data (FIG. 3) show that all tested Mabs do also recognize primate (Cynomolgus Macaque and baboon) T cells. Rat T cells were negative.

Antibody-Dependent Cellular Cytotoxicity (ADCC) of Anti-Human CD127 Mabs

Figure 4A:
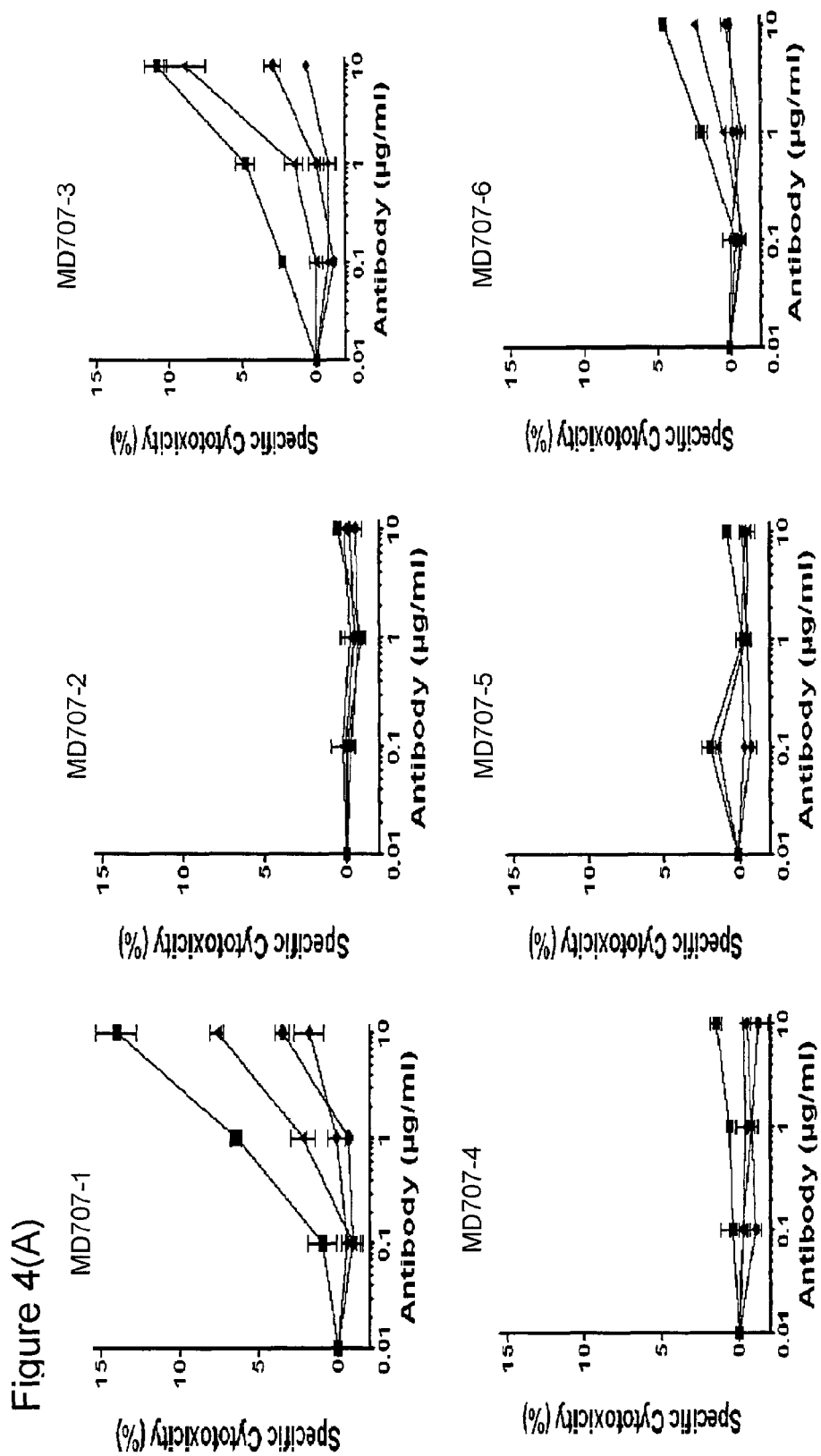
Figure 4B:
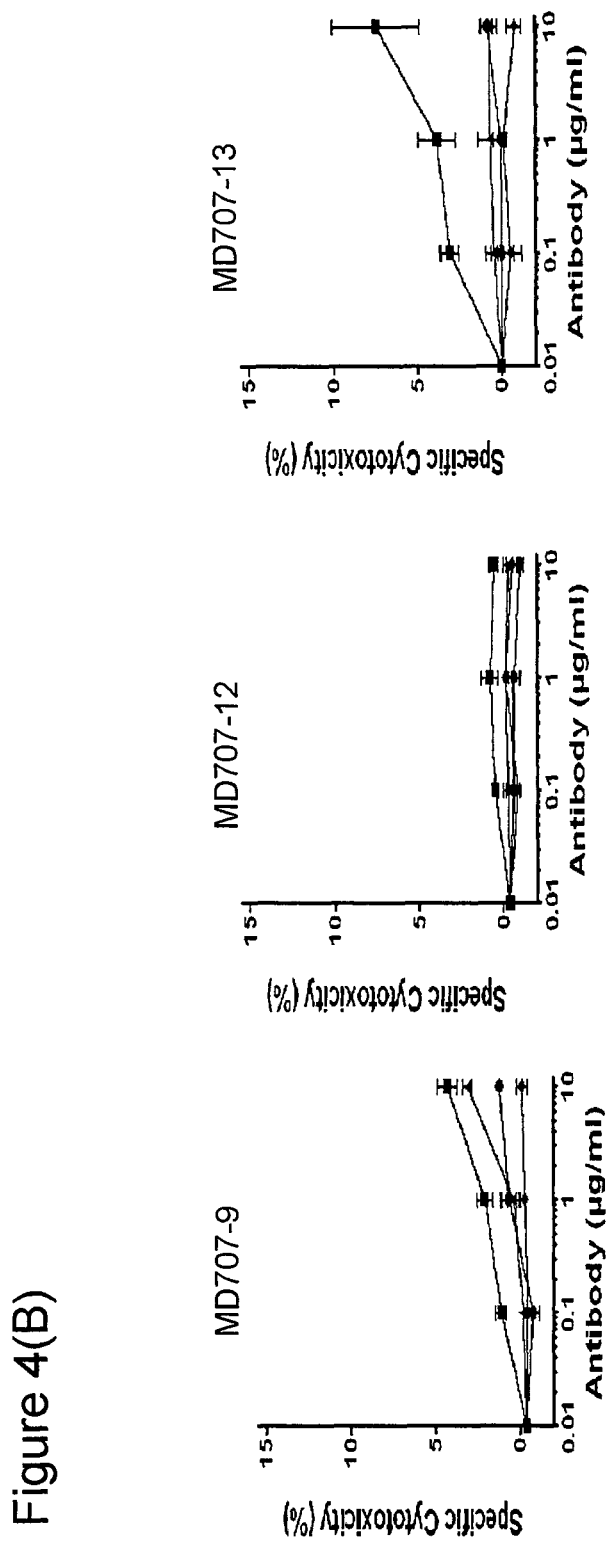

ADCC refers to as the binding of an antibody to an epitope expressed on target cells and the subsequent Fc-dependent recruitment of effector immune cells expressing Fc receptors (essentially NK cells and activated lymphocytes), resulting in the killing of target cells mainly by granzyme/perforin-based mechanisms Mabs shown in table 1 were used in ADCC assays. Lymphokine activated killer cells (LAK) of rat origin (because the Mab was obtained from rat splenocytes) were used as effector cells to kill target human T cells expressing CD127, in the presence of Mabs. The data shown in FIG. 4 revealed that only Mabs 7MD07-1, 3, 6, 9 and 13 did elicit ADCC. Interestingly, there is no direct correlation between affinity, binding and ADCC properties, indicating that ADCC properties could not be predicted from binding analyses.

Antagonistic Properties of Anti-Human CD127 Mabs

Figure 5B:
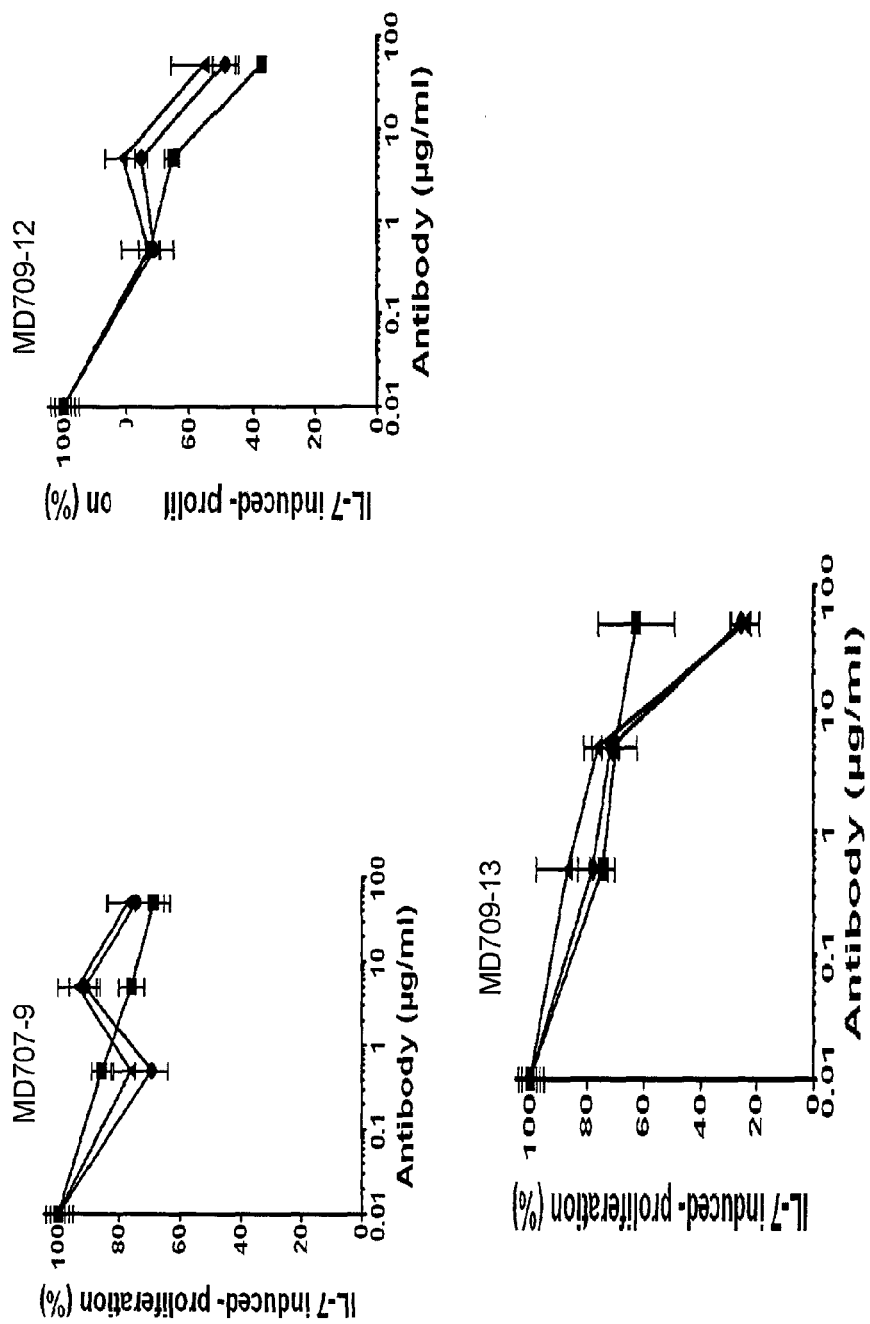

The ability of a given Mab directed to a receptor to antagonize binding of a ligand to that receptor probably depends on the ability of that Mab to target an epitope that is used by the ligand for docking into the receptor. It might also depend on the ability of the Mab to modify target conformation and thereby modify the binding properties of the receptor. The data shown in FIG. 5 revealed that Mabs MD707-1, 2, 3, 4, 5, 12 and 13 were able to prevent IL-7-mediated T cell growth whereas MD707-6 and 9 did so only in a limited extent.

Nucleotides and Aminoacid Sequences of Anti-Human CD127 Mabs

Figure 7:
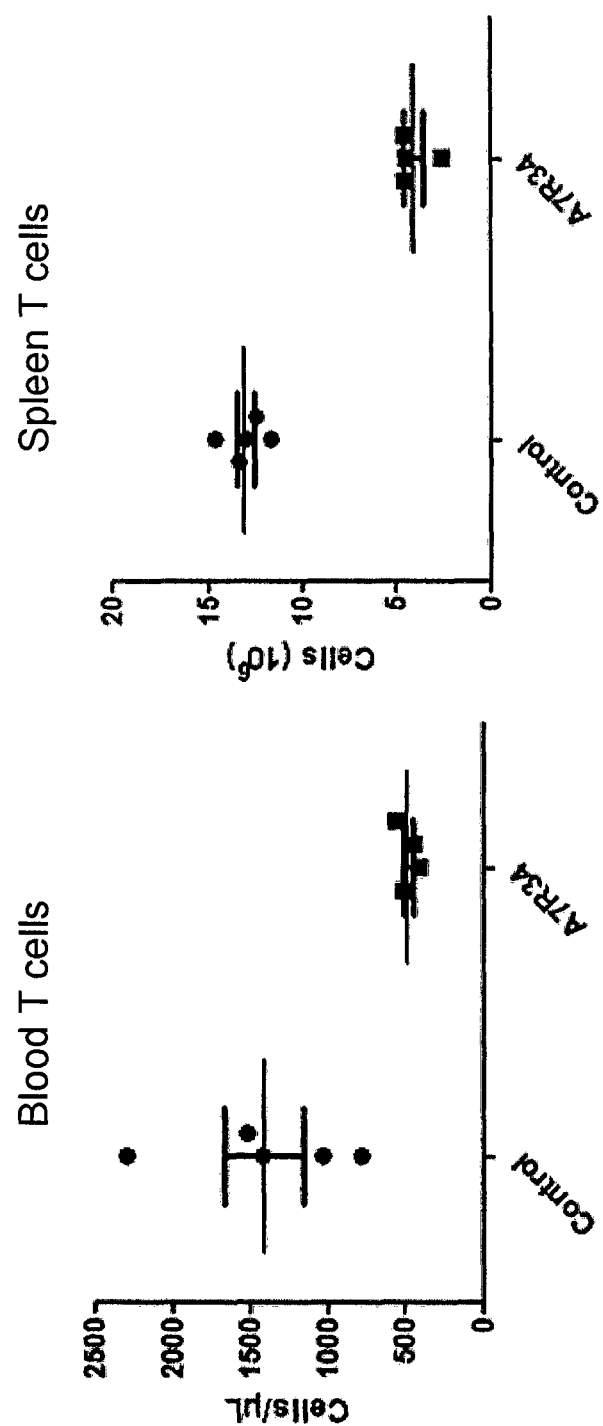
Figure 8:
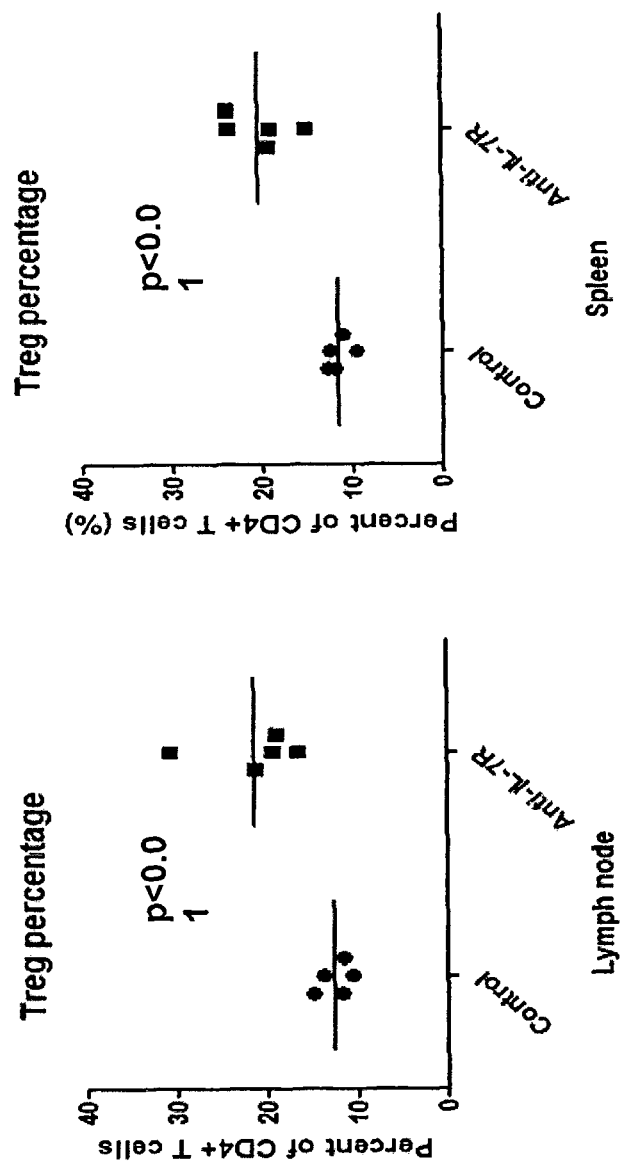

VH and VL regions of the MD707 clones were sequenced using the RACE PCR technology. Briefly, total RNA was extracted, reverse transcribed and the resulting cDNA was poly-adenylated at the 3' end of the molecules using dATP and the terminal transferase enzyme. A first 35-cycle PCR reaction was performed using a oligo dT anchor primer and Herculease enzyme (Stratagene). A second 35-cycle PCR was performed using nested PCR anchor primers. The resulting PCR product was then TA-cloned in *E. Coli* and after selection on ampicillin, resulting colonies were screened by restriction enzyme profiling and inserted cDNA sequenced. Nucleotidic sequences and deduced amino acid sequences are shown on FIG. 6 and in the Sequence Listing 2. Activity of Surrogate Anti-CD127 Monoclonal Antibodies in Depletion of T cells Surrogate Anti-Human CD127 Mabs Deplete Teff Cells and Increase Treg/Teff Ratios To illustrate how anti-CD127 Mab do impact T cells, 9 week-old male Balb/c mice (H-2b) received anti-CD127 Mabs (clone A7R34 directed against mouse CD127), 400 µg IP every other day during 21 days. It was observed that T cells, as a result, were depleted in blood and in the spleen (FIG. 7) (as well as in the lymph nodes and the thymus, data not shown). Interestingly, in the residual cells, the ratio of Treg cells, normally of about 10%, rose up to 20%, indicating a preferential depletion of Tell versus Treg cells (FIG. 8).

Surrogate Anti-Human CD127 Mabs Prevent Pancreatic Islet Graft Rejection

Figure 9:
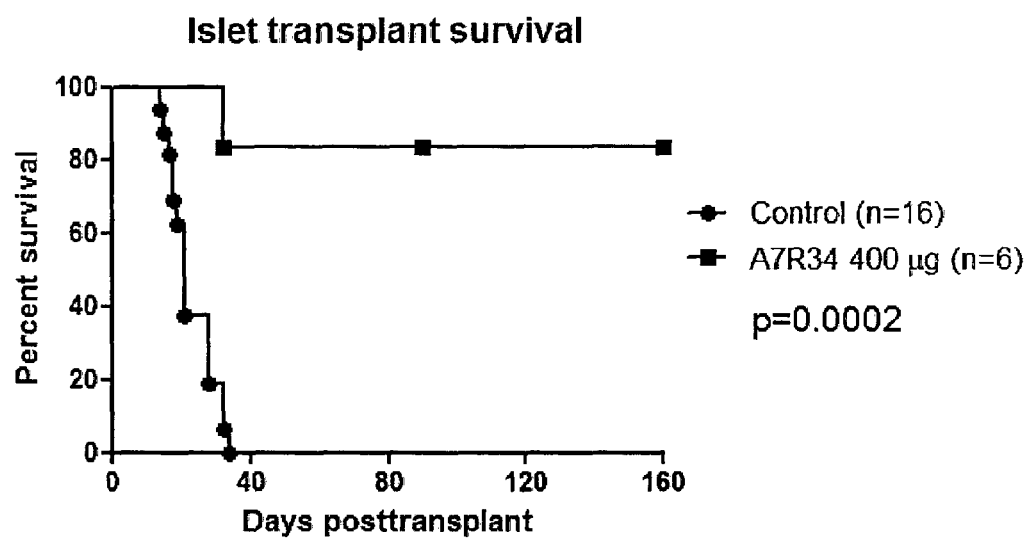

To understand how anti-CD127 Mabs might modulate allograft rejection, 7 to 9 week-old male Balb/c mice (H-2b) were rendered diabetic by streptozotocin 250 mg/kg IP 5-10 days before implantation of pancreatic ilets from C57BL/6 mice (H-2d). It was observed that control mice had median graft survival of 21 days (range: 14-34 days) whereas 5 of 6 treated mice had indefinite graft survival (>160 days) (p=0.0002, log-rank test; FIG. 9).

Surrogate Anti-Human CD127 Mabs Prevent and Cure Diabetes in NOD Mice

Figure 10:
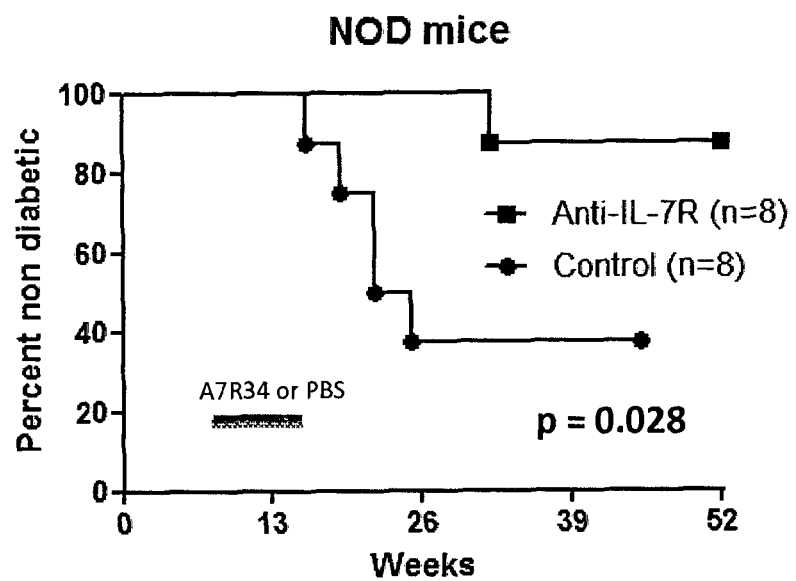

To understand how anti-CD127 Mabs might modulate an autoimmune disease, female non-obese diabetic (NOD) mice of 6 weeks of age were treated with an anti-IL-7R monoclonal antibody (clone A7R34) 400 µg IP 3 times per week for 8 wks from week 8 to week 16 of age. Control group received PBS at the same volume and same schedule. Results, shown on FIG. 10, demonstrated that treated mice were mostly protected against diabetes whereas more than 60% of control animals developed diabetes within the first 26 weeks of age.

II) ADCC Activity of a Chimeric Anti-CD127 Antibody

A chimeric antibody prepared with MD707-3 anti-CD127 Mab was obtained by substituting the Fc fragment of the original rat antibody, by a human Fc fragment.

For this chimeric antibody, the effector cells were fresh primary human NK cells isolated from peripheral blood mononuclear cells by negative selection using magnetic beads (NK isolation kit, Miltenyi Biotec, Bergisch Gladbach, Germany) using an AutoMACS cell sorting instrument. NK cells were incubated over-night at 37° C., 5% $CO_2$, in RPMI 1640 Medium (Life Technologies, Carlsbad, Calif.) complemented with 10% FBS (Life Technologies), 100 IU/ml penicillin (Life Technologies), 0.1 mg/ml streptomycin (Life Technologies), 2 mM L-glutamine (Life Technologies) and 150 IU/ml of human IL-2 (Roche, Basel, Switzerland).

The target cells were labeled with 100 µCi (3.7 MBq) of $^{51}Cr$ (PerkinElmer) for 1 h at 37° C. and washed three times with culture medium. Target cells were incubated with diluted antibodies or with excipient (culture medium) for 15 min at room temperature and 10 000 cells were placed in a 96-well U-bottom plate. Effector T cells were added at the indicated E:T (effector:target) cell ratio (final volume: 200 µl) for a 4 or 18 hours incubation period at 37° C. A total of 25 µl of the supernatant was then harvested and counted in a gamma counter (Packard Instrument).

Figure 11:
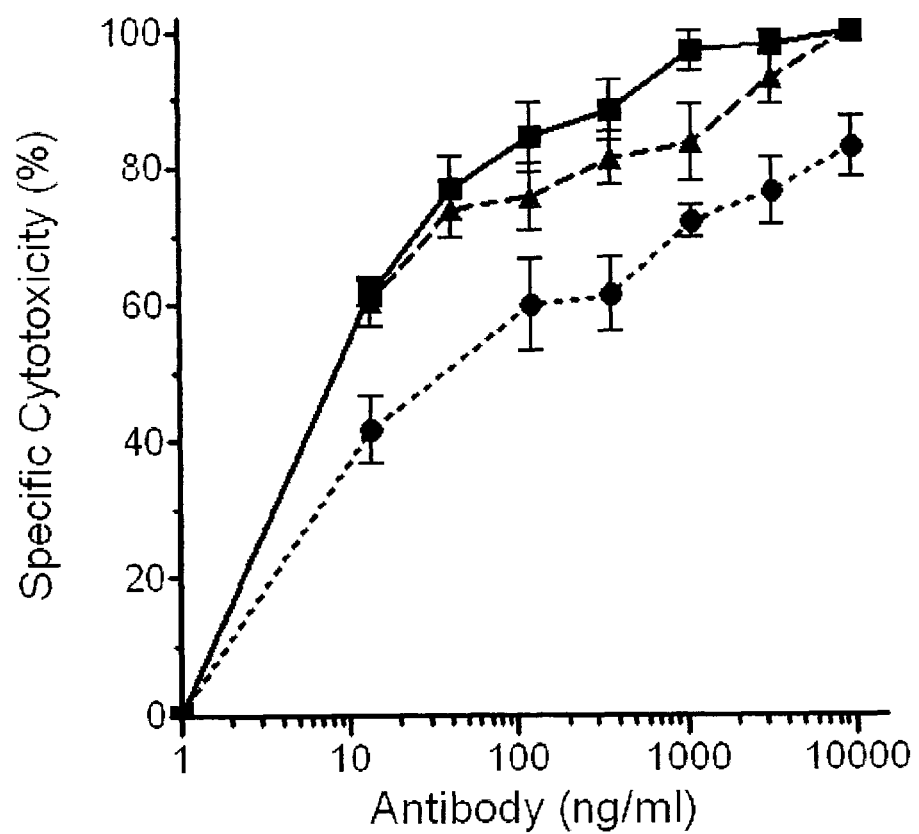
Figure 12:
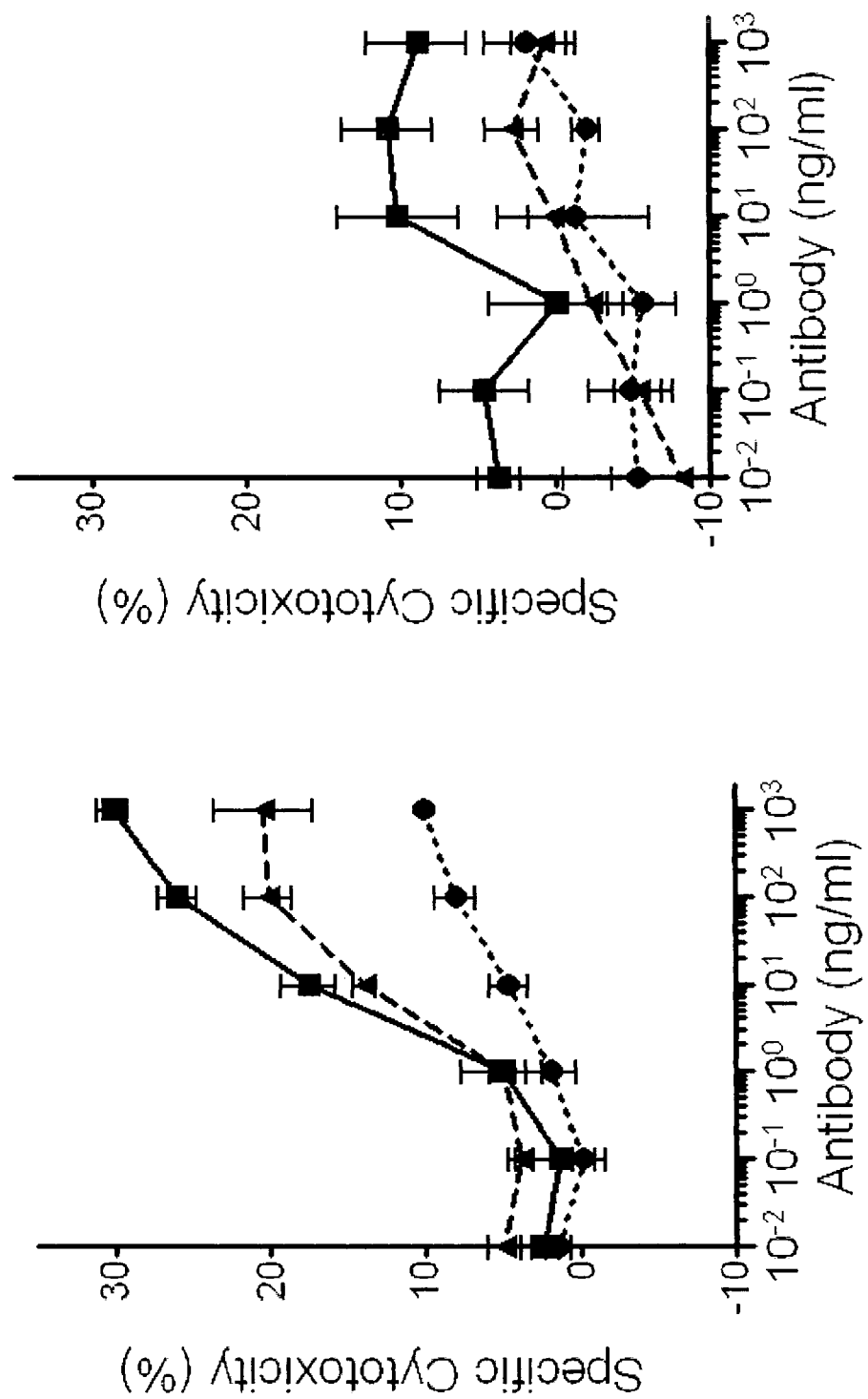

The results of the assays are disclosed on FIGS. 11 and 12.

The invention claimed is:

1. An antibody or a functional fragment thereof whose antigen-binding site comprises a Variable Heavy chain and a Variable Light chain, wherein the Variable Heavy chain comprises the following polypeptides:
  (a) (i) VHCDR 1 having the amino acid sequence of SEQ ID No 38;
    (ii) VHCDR 2 having the amino acid sequence of SEQ ID No 40; and
    (iii) VHCDR 3 having the amino acid sequence of SEQ ID No 42; or
  (b) VH having amino acid sequence from position 22 to position 135 of SEQ ID No 34; and
wherein the Variable Light chain comprises the following polypeptides:
  (c) (i) VLCDR 1 having the amino acid sequence of SEQ ID No 44;
    (ii) VLCDR 2 having the amino acid sequence of SEQ ID No 46; and
    (iii) VLCDR 3 having the amino acid sequence of SEQ ID No 48; or
  (d) VL having amino acid sequence from position 22 to position 129 of SEQ ID No 36.

2. The antibody or the functional fragment thereof according to claim 1 which binds the alpha chain of the receptor to IL-7 (designated CD127), and which exhibits Antibody-Dependent Cellular Cytotoxicity (ADCC) or both ADCC and Complement-Dependent Cytotoxicity (CDC) against human CD127 positive cells.

3. The antibody or the functional fragment thereof according to claim 2, wherein the human CD127 positive cells are human T cells expressing CD127.

4. The antibody or the functional fragment thereof according to claim 1, which further has antagonist properties toward interleukin 7 (IL-7) thereby antagonizing access of IL-7 to CD127 on human CD127 positive cells.

5. The antibody according to claim 1, wherein the antibody is a humanized monoclonal antibody or a chimeric monoclonal antibody.

6. The antibody or the functional fragment thereof according to claim 5, wherein the antibody is a humanized antibody, wherein amino acid residue(s) present in constant region(s) of the antibody are substituted by amino acid residue(s) having corresponding location(s) in human antibodies according to standard definition and numbering, and wherein the substitution level is from 1% to 20% of the residues in said constant regions.

7. An antibody or a functional fragment thereof selected from the group consisting of:
  (a) an antibody produced by hybridoma MD707-13 deposited at the CNCM under No I-4533 or a functional fragment thereof; and
  (b) an antibody expressed by recombinant eukaryotic cells, which are recombined with nucleic acid molecule(s) identical to cDNA corresponding to RNA expressed in hybridoma MD707-13 deposited at the CNCM under No I-4533 that encodes the antibody of (a), or a functional fragment thereof.

8. A chimeric molecule comprising an antibody or a functional fragment thereof whose antigen-binding site comprises a Variable Heavy chain and a Variable Light chain, wherein the Variable Heavy chain comprises the following polypeptides:
  (a) (i) VHCDR 1 having the amino acid sequence of SEQ ID No 38;
    (ii) VHCDR 2 having the amino acid sequence of SEQ ID No 40; and
    (iii) VHCDR 3 having the amino acid sequence of SEQ ID No 42; or
  (b) VH having amino acid sequence from position 22 to position 135 of SEQ ID No 34; and
wherein the Variable Light chain comprises the following polypeptides:
  (c) (i) VLCDR 1 having the amino acid sequence of SEQ ID No 44;
    (ii) VLCDR 2 having the amino acid sequence of SEQ ID No 46; and
    (iii) VLCDR 3 having the amino acid sequence of SEQ ID No 48; or
  (d) VL having amino acid sequence from position 22 to position 129 of SEQ ID No 36;
wherein said antibody or functional fragment is associated with a functionally different molecule, and wherein said chimeric molecule is either a fusion chimeric protein or a conjugate resulting from covalent attachment of a chemical group or molecule.

9. The chimeric molecule according to claim 8 wherein said chimeric molecule is a conjugate resulting from covalent attachment of a PEG polymer or of a labeled antibody.

10. A pharmaceutical composition comprising a pharmaceutical vehicle and an antibody or a functional fragment thereof whose antigen-binding site comprises a Variable Heavy chain and a Variable Light chain, wherein the Variable Heavy chain comprises the following polypeptides:
  (a) (i) VHCDR 1 having the amino acid sequence of SEQ ID No 38;
    (ii) VHCDR 2 having the amino acid sequence of SEQ ID No 40; and
    (iii) VHCDR 3 having the amino acid sequence of SEQ ID No 42; or
  (b) VH having amino acid sequence from position 22 to position 135 of SEQ ID No 34; and
wherein the Variable Light chain comprises the following polypeptides:
  (c) (i) VLCDR 1 having the amino acid sequence of SEQ ID No 44,
    (ii) VLCDR 2 having the amino acid sequence of SEQ ID No 46, and
    (iii) VLCDR 3 having the amino acid sequence of SEQ ID No 48; or
  (d) VL having amino acid sequence from position 22 to position 129 of SEQ ID No 36.

11. The pharmaceutical composition of claim 10, wherein the pharmaceutical composition is formulated for controlling CD127+ cells survival or expansion when administered to a human patient.

12. The pharmaceutical composition of claim 11, wherein the pharmaceutical composition is formulated for controlling CD4+ and CD8+ memory T cells survival or expansion when administered to a human patient.

13. The pharmaceutical composition according to claim 10 further comprising a compound having a therapeutic immunomodulator effect on cells involved in allergy or autoimmunity.

* * * * *